US012752098B2

(12) United States Patent
Ivers et al.

(10) Patent No.: US 12,752,098 B2
(45) Date of Patent: Oct. 6, 2026

(54) REAL-TIME DETECTION OF R-WAVES AND METHODS THEREFOR

(71) Applicant: NuPulseCV, Inc., Raleigh, NC (US)

(72) Inventors: Douglas Edward Ivers, Cary, NC (US); Guruprasad Anapathur Giridharan, Louisville, KY (US); Nagarjuna Reddy Chinta, Apex, NC (US)

(73) Assignee: NuPulseCV, Inc., Raleigh, NC (US)

( * ) Notice: Subject to any disclaimer, the term of this patent is extended or adjusted under 35 U.S.C. 154(b) by 237 days.

(21) Appl. No.: 18/222,255

(22) Filed: Jul. 14, 2023

(65) Prior Publication Data

US 2025/0018170 A1 Jan. 16, 2025

(51) Int. Cl.

| | |
|---|---|
| ***A61M 60/161*** | (2021.01) |
| ***A61B 5/352*** | (2021.01) |
| ***A61M 60/139*** | (2021.01) |
| ***A61M 60/295*** | (2021.01) |
| ***A61M 60/497*** | (2021.01) |

(52) U.S. Cl.

CPC ........ *A61M 60/161* (2021.01); *A61M 60/139* (2021.01); *A61M 60/295* (2021.01); *A61M 60/497* (2021.01); *A61B 5/352* (2021.01); *A61M 2205/50* (2013.01); *A61M 2230/04* (2013.01)

(58) Field of Classification Search

CPC .............. A61M 60/161; A61M 60/497; A61M 60/295; A61M 60/139; A61M 60/352; A61M 2205/50; A61M 2230/04

See application file for complete search history.

(56) References Cited

U.S. PATENT DOCUMENTS

| | | | |
|---|---|---|---|
| 2,877,873 | A | 3/1959 | Ayers, Jr. |
| 3,585,983 | A | 6/1971 | Kantrowitz et al. |
| 3,692,018 | A | 9/1972 | Goetz et al. |
| 3,720,199 | A | 3/1973 | Rishton et al. |
| 3,924,634 | A | 12/1975 | Taylor et al. |
| 3,964,470 | A | 6/1976 | Trombley |
| 4,038,625 | A | 7/1977 | Tompkins et al. |
| 4,051,840 | A | 10/1977 | Kantrowitz et al. |
| 4,146,044 | A | 3/1979 | Dow |
| 4,185,617 | A | 1/1980 | Hutchins |

(Continued)

FOREIGN PATENT DOCUMENTS

| | | |
|---|---|---|
| DE | 3722161 A1 | 1/1989 |
| EP | 0228787 A1 | 7/1987 |

(Continued)

OTHER PUBLICATIONS

BARD Dynaflow Bypass Grafts Instructions for Use (Dec. 2007), 44 pages.

(Continued)

*Primary Examiner* — Lindsey G Wehrheim

(57) ABSTRACT

A drive unit system for operating a cardiac assist device is disclosed. The drive unit system may include an R-wave detection module that makes a speculative detection of an R-wave associated with a received electrocardiogram (ECG) signal of a patient's heart and a conservative detection of the R-wave. The drive unit system includes a drive unit that may be coupled to the cardiac assist device and may operate the cardiac assist device based on the speculative detection and the conservative detection.

57 Claims, 17 Drawing Sheets

(56) References Cited

U.S. PATENT DOCUMENTS

| | | | |
|---|---|---|---|
| 4,276,874 | A | 7/1981 | Wolvek et al. |
| 4,277,706 | A | 7/1981 | Isaacson |
| 4,327,709 | A | 5/1982 | Hanson et al. |
| 4,527,549 | A | 7/1985 | Gabbay |
| 4,540,404 | A | 9/1985 | Wolvek |
| 4,634,430 | A | 1/1987 | Polaschegg |
| 4,785,795 | A | 11/1988 | Singh |
| 4,902,272 | A | 2/1990 | Milder et al. |
| 4,931,036 | A | 6/1990 | Kanai et al. |
| 4,994,018 | A | 2/1991 | Saper |
| 5,052,934 | A | 10/1991 | Carey et al. |
| 5,098,397 | A | 3/1992 | Svensson et al. |
| 5,147,318 | A | 9/1992 | Hohn |
| 5,176,619 | A | 1/1993 | Segalowitz |
| 5,350,413 | A | 9/1994 | Miller |
| 5,350,876 | A | 9/1994 | Drent et al. |
| 5,433,700 | A | 7/1995 | Peters |
| 5,509,902 | A | 4/1996 | Raulerson |
| 5,683,347 | A | 11/1997 | Miyata et al. |
| 5,782,645 | A | 7/1998 | Stobie et al. |
| 5,820,542 | A | 10/1998 | Dobak, III et al. |
| 5,833,655 | A | 11/1998 | Freed et al. |
| 5,876,367 | A | 3/1999 | Kaganov et al. |
| 5,904,646 | A | 5/1999 | Jarvik |
| 6,030,336 | A | 2/2000 | Franchi |
| 6,132,363 | A | 10/2000 | Freed et al. |
| 6,210,318 | B1 | 4/2001 | Lederman |
| 6,241,706 | B1 | 6/2001 | Leschinsky et al. |
| 6,245,008 | B1 | 6/2001 | Leschinsky et al. |
| 6,406,422 | B1 | 6/2002 | Landesberg |
| 6,453,195 | B1 | 9/2002 | Thompson |
| 6,468,200 | B1 | 10/2002 | Fischi |
| 6,497,678 | B2 | 12/2002 | Schock |
| 6,530,876 | B1 | 3/2003 | Spence |
| 6,656,153 | B1 | 12/2003 | Sakai et al. |
| 6,945,926 | B2 | 9/2005 | Trumble |
| 6,961,448 | B2 | 11/2005 | Nichols et al. |
| 7,059,338 | B1 | 6/2006 | Kincaid et al. |
| 7,374,531 | B1 | 5/2008 | Kantrowitz |
| 7,468,050 | B1 | 12/2008 | Kantrowitz |
| 7,494,459 | B2 | 2/2009 | Anstadt et al. |
| 7,520,850 | B2 | 4/2009 | Brockway |
| 7,574,262 | B2 | 8/2009 | Haugland et al. |
| 7,632,263 | B2 | 12/2009 | Denoth et al. |
| 7,666,167 | B2 | 2/2010 | Bierman |
| 7,766,881 | B2 | 8/2010 | Reinmann |
| 7,892,162 | B1 | 2/2011 | Jeevanandam et al. |
| 7,935,096 | B2 | 5/2011 | Johansson et al. |
| 7,988,674 | B2 | 8/2011 | Adams et al. |
| 8,066,628 | B1 | 11/2011 | Jeevanandam et al. |
| 8,152,769 | B2 | 4/2012 | Douglas et al. |
| 8,323,174 | B2 | 12/2012 | Jeevanandam et al. |
| 8,326,421 | B2 | 12/2012 | Jeevanandam et al. |
| 8,545,382 | B2 | 10/2013 | Suzuki et al. |
| 8,574,204 | B2 | 11/2013 | Bourne et al. |
| 8,608,637 | B2 | 12/2013 | Jeevanandam et al. |
| 8,684,905 | B2 | 4/2014 | Jeevanandam et al. |
| 9,125,981 | B2 | 9/2015 | Mann et al. |
| 9,265,871 | B2 | 2/2016 | Jeevanandam et al. |
| 9,592,328 | B2 | 3/2017 | Jeevanandam et al. |
| 9,839,734 | B1 | 12/2017 | Menon et al. |
| 10,137,230 | B2 | 11/2018 | Novack |
| 12,156,978 | B2 | 12/2024 | Smith et al. |
| 2001/0035046 | A1 | 11/2001 | Williams |
| 2002/0169413 | A1 | 11/2002 | Keren et al. |
| 2003/0074144 | A1 | 4/2003 | Freed et al. |
| 2003/0083539 | A1 | 5/2003 | Leschinsky |
| 2003/0163147 | A1 | 8/2003 | Rabiner et al. |
| 2004/0152945 | A1 | 8/2004 | Kantrowitz et al. |
| 2004/0215050 | A1 | 10/2004 | Morello |
| 2004/0249361 | A1 | 12/2004 | Denoth et al. |
| 2005/0014991 | A1 | 1/2005 | Sugiura |
| 2005/0150873 | A1 | 7/2005 | Schmitt-Walter et al. |
| 2005/0192604 | A1 | 9/2005 | Carson et al. |
| 2006/0063965 | A1 | 3/2006 | Aboul-Hosn et al. |
| 2007/0005010 | A1 | 1/2007 | Mori et al. |
| 2007/0161916 | A1 | 7/2007 | Zantos et al. |
| 2007/0191779 | A1 | 8/2007 | Shubayev et al. |
| 2008/0161637 | A1 | 7/2008 | Sun et al. |
| 2008/0183136 | A1 | 7/2008 | Lenker et al. |
| 2009/0131741 | A1 | 5/2009 | Kantrowitz |
| 2010/0228077 | A1 | 9/2010 | Lenker et al. |
| 2012/0010886 | A1 | 1/2012 | Razavilar |
| 2012/0149970 | A1 | 6/2012 | Jeevanandam et al. |
| 2012/0149971 | A1* | 6/2012 | Jeevanandam ..... A61M 60/515 600/17 |
| 2013/0066365 | A1 | 3/2013 | Belson et al. |
| 2013/0331638 | A1 | 12/2013 | Cameron et al. |
| 2015/0051436 | A1 | 2/2015 | Spanier et al. |
| 2015/0065786 | A1 | 3/2015 | Jeevanandam et al. |
| 2015/0157842 | A1 | 6/2015 | Gill et al. |
| 2015/0258261 | A1 | 9/2015 | Novack |
| 2016/0136343 | A1 | 5/2016 | Anagnostopoulos |
| 2016/0158426 | A1 | 6/2016 | Jeevanandam et al. |
| 2016/0175502 | A1 | 6/2016 | McSweeney et al. |
| 2017/0021071 | A1 | 1/2017 | Cotter |
| 2017/0173237 | A1 | 6/2017 | Pfeifer et al. |
| 2017/0216506 | A1 | 8/2017 | Jeevanandam et al. |
| 2018/0055981 | A1 | 3/2018 | Smith et al. |
| 2018/0099078 | A1 | 4/2018 | Tuseth et al. |
| 2018/0116843 | A1 | 5/2018 | Schreck et al. |
| 2018/0350468 | A1 | 12/2018 | Friedman et al. |
| 2019/0184077 | A1 | 6/2019 | Novack |
| 2019/0192164 | A1 | 6/2019 | Parekh et al. |
| 2020/0069855 | A1 | 3/2020 | Matthes et al. |
| 2020/0129685 | A1 | 4/2020 | Gellman et al. |
| 2020/0182387 | A1 | 6/2020 | Morrissey |
| 2020/0360663 | A1 | 11/2020 | Smith et al. |
| 2022/0032033 | A1 | 2/2022 | Besselink et al. |
| 2023/0001826 | A1 | 1/2023 | Sirois et al. |
| 2023/0069771 | A1 | 3/2023 | Ivers |
| 2024/0082563 | A1 | 3/2024 | Hall et al. |
| 2024/0082564 | A1 | 3/2024 | Woolley et al. |
| 2024/0082565 | A1 | 3/2024 | Woolley et al. |
| 2024/0382739 | A1 | 11/2024 | Ivers |
| 2025/0018153 | A1 | 1/2025 | Smith et al. |
| 2025/0387614 | A1 | 12/2025 | Chinta et al. |

FOREIGN PATENT DOCUMENTS

| | | | |
|---|---|---|---|
| EP | 2548593 | A1 | 1/2013 |
| EP | 2744403 | B1 | 3/2017 |
| GB | 2050175 | A | 1/1981 |
| JP | H0724060 | A | 1/1995 |
| JP | 2000513244 | A | 10/2000 |
| JP | 2002518106 | A | 6/2002 |
| JP | 2005000434 | A | 1/2005 |
| JP | 2009082664 | A | 4/2009 |
| JP | 2013508094 | A | 3/2013 |
| JP | 2014198250 | A | 10/2014 |
| JP | 2018161324 | A | 10/2018 |
| JP | 2018538120 | A | 12/2018 |
| JP | 2019170691 | A | 10/2019 |
| WO | WO-9111208 | A1 | 8/1991 |
| WO | WO-1997030740 | A1 | 8/1997 |
| WO | WO-2011050279 | A2 | 4/2011 |
| WO | WO-2012101267 | A1 | 8/2012 |
| WO | WO-2013180286 | A1 | 12/2013 |
| WO | WO-2015034955 | A1 | 3/2015 |
| WO | WO-2015142753 | A1 | 9/2015 |
| WO | WO-2017136537 | A1 | 8/2017 |
| WO | WO-2018039461 | A1 | 3/2018 |
| WO | WO-2019152882 | A1 | 8/2019 |
| WO | WO-2023014659 | A1 | 2/2023 |

OTHER PUBLICATIONS

"BioSpan: Segmented Polyurethane (SPU), DSM Bright Science. Brighter Living", (2014, pub month not available), 2 pages. [Retrieved from Internet on Oct. 10, 2017 at www.dsm.com/markets/medical/en_US/ [g] products-paqe/products-biostable-polyu rethanes/product-pu-biospan-spu].

(56) References Cited

OTHER PUBLICATIONS

Chen, et al., "Design and operation of a fast, thin-film thermocouple probe on a turbine engine", American Institute of Aeronautics and Astronautics, (Jul. 30, 2014), 20 pages. [Retrieved from Internet on May 29, 2025; https://ntrs.nasa.gov/api/citations/20140017302/ downloads/20140017302.pdf].
Chen, Z. et al. "Interaction of fibrinogen with surfaces of end-group-modified polyurethanes: a surface-specific sum-frequency-generation vibrational spectroscopy study", Journal of Biomedical Materials Research, (Aug. 2, 2002), vol. 62(2), pp. 254-264.
Jeevanandam et al. "Circulatory Assistance with a Permanent Implantable IABP: Initial Human Experience", Circulation, (Sep. 24, 2002), 106, pp. I-183-I-188 (6 pages).
Kantrowitz et al. "A Mechanical Auxiliary Ventricle: Histologic Responses to Long- Term, Intermittent Pumping in Calves" ASAIO Journal, (Jul. 1995), 41(34), pp. M340-M345.
Li et al. "The Kantrowitz Cardiovad System Can Be Deactivated for Two Months and Reactivated Without Thromboembolism" ASAIO Journal, (Mar.-Apr. 2000), vol. 46, No. 2, p. 205 (3 pages total).
Tsutsui T et al., "Effect of Weaning Process of Mechanical Circulatory Support on Circulatory Autonomic Nervous System Evaluated by Power Spectral Analysis of Arterial Pressure Waves," The International Journal of Artificial Organs, vol. 28, No. 9, Oct. 2005, p. 918.

* cited by examiner

REAL-TIME DETECTION OF R-WAVES AND METHODS THEREFOR

BACKGROUND

The disclosure relates generally to medical devices, and more particularly to systems and methods related to the operation of cardiac assist devices (CADs), based on physiological measurements. About 5.7 million adults in the United States have heart failure, according to the U.S. Centers for Disease Control and Prevention website. Each year, about 100,000 people nationally are diagnosed with advanced heart failure and require some sort of mechanical support, e.g., via a CAD. In some instances, a CAD may perform ventricular assistance, counterpulsation therapy or copulsation therapy. In general terms, counterpulsation is a ventricular support technique that assists circulation and decreases the work of the heart by increasing aortic blood pressure during diastole (i.e., diastolic aortic pressure) relative to unassisted diastolic aortic blood pressure (i.e., without counterpulsation) and by decreasing aortic blood pressure during systole (i.e., systolic aortic blood pressure) relative to unassisted systolic aortic blood pressure (i.e., without counterpulsation). For its part, copulsation is a ventricular support technique that increases systolic aortic blood pressure relative to unassisted systolic aortic blood pressure.

There are numerous CADs capable of delivering different levels of support at different levels of invasiveness to treat cardiac malfunction. Exemplary CADs include counterpulsation devices (i.e., devices that are specific to counterpulsation modalities and that are implanted in the vasculature) and ventricle assist devices (VADs) that are at least partially implanted in the ventricle.

Counterpulsation devices include intra-aortic balloon pumps, patch devices, cuff devices, and other pump devices anastomosed to a large blood vessel. An intra-aortic balloon pump or IABP may be positioned inside the aorta, typically in the proximal descending aorta. The balloon pump (typically 25-50 milliliters in capacity) may be inflated and deflated in synchrony with the contraction of the left ventricle, thereby performing counterpulsation therapy. The IABP may be inflated during diastole, thereby increasing diastolic aortic blood pressure relative to the unassisted diastolic aortic blood pressure and driving blood in the ascending aorta and aortic arch into the coronary arteries to supply oxygen to the heart muscle. The IABP may be deflated during systole, as the left ventricle contracts, thereby decreasing systolic aortic blood pressure relative to unassisted systolic aortic blood pressure and decreasing the afterload (i.e., the effort required of the heart to push blood into the aorta).

Other counterpulsation devices operate similarly. For example, patch devices are generally implanted on the descending thoracic aorta. A longitudinal incision may be performed the patch device may be sutured to the lateral aspect of the descending thoracic aorta. The patch device may include an elongated inflatable valve-less polyurethane patch powered by an external compressor. The patch may be inflated and deflated in time with the contraction of the left ventricle, thereby performing counterpulsation therapy, similar to the manner described above with respect to the balloon pump. An example of a patch device is the Kantrowitz CardioVad.

Similarly, cuff devices may be wrapped around the ascending aorta and may have a membrane (e.g., a balloon) that is positioned against the vessel's external wall. The positive and negative pressure of the membrane facilitates counterpulsation. An example of a cuff device is the Sunshine C-Pulse® heart assist system.

Blood pump devices may be implanted into a pocket below the petoralis muscle on the anterior chest and attached to a vascular graft anastomosed to the subclavian artery. The blood pump device may include a reservoir that fills with blood during systole (thereby reducing systolic aortic blood pressure relative to unassisted systolic aortic blood pressure) and empties during diastole (thereby increasing diastolic aortic blood pressure relative to unassisted diastolic aortic blood pressure). An example of such a blood pump device is the Symphony Counter Pulsation Device (CPD). Other blood pump devices exist including so-called para-aortic blood pumps and disposable blood pumps for life support during cardiac surgical procedures (e.g., the PulseCath iVAC or PUCA pump). Both operate similarly to the Symphony CPD. Para-aortic blood pumps are anastomosed to the descending aorta and the PulseCath iVAC or PUCA pumps consist of a catheter containing a two-way value connected to a pump that operates to aspirate blood from the left ventricle in systole (decreasing systolic aortic blood pressure relative to unassisted systolic aortic blood pressure) and push the blood back into the aorta during diastole (increasing diastolic aortic blood pressure relative to unassisted diastolic aortic blood pressure).

Notably, some counterpulsation devices can be configured or re-configured to function as a copulsation device, if implanted in the ventricle. As noted above, in copulsation the device will operate to increase aortic blood pressure (relative to the unassisted aortic blood pressure) during systole.

VADs are CADs that assist cardiac circulation by pumping blood. Generally, blood is drawn out of the left ventricle, into the pump, then into the aorta and on to the body and/or out of the right ventricle, into the pump, then into the pulmonary artery, and on to the lungs to pick up oxygen. VAD pumps can be external or paracorpeal, or they can be implanted (e.g., connected to the left ventricle and/or right ventricle via open heart surgery or placed into position using a catheter). VADs are generally characterized as being pulsatile flow or continuous-flow. Continuous-flow VADs are sometimes called CF-VADs and are generally driven by an impeller or rotor. Some VADs can operate in counterpulsation or copulsation modalities if the VAD is synchronized to the heart cycle. If the VAD is not synchronized to the heart cycle, the VAD may be said to operate asynchronously.

Current VADs include the CorWave left ventricle assist device (LVAD), the Abbot HeartMate 3 LVAD, the Abbot HeartMate 2 LVAD, the Medtronic HeartWare HVAD, the Abiomed Impella® pump and the EVAHEART®2 LVAD. The CorWave LVAD uses a wave membrane whereas the other identified VADs are CF-VADs. Some CF-VADs use a valveless axial pump with a variable magnetic field that spins an impeller that produces a continuous outflow directed in parallel to the axis of rotation (i.e., so called axial flow pumps). Other VADs use centrifugal pumps with magnetic or hydrodynamic levitation of the impeller with non-contact bearings and outflow directed perpendicular to the axis of rotation (i.e., so-called centrifugal pumps). The Abiomed Impella pump is an example of a VAD with a catheter-based micro-axial rotary pump. It is inserted into the patient's femoral artery is then guided into the left ventricle. The Impella pulls blood from the left ventricle to the ascending aorta. Taking the Abiomed Impella as an example, this VAD can be deployed in copulsation by driving the rotor at a higher rpm during systole and at lower rpm during diastole. The result is that systolic aortic blood pressure is increased as compared to an unassisted systolic aortic blood pressure. The Abiomed Impella can also be deployed in counterpulsation by driving the rotor at higher rpm during diastole and at lower rpm during systole. Like the counterpulsation devices, this results in an increased diastolic aortic blood pressure (as compared to an unassisted diastolic aortic blood pressure and a decreased systolic aortic blood pressure (as compared to an unassisted systolic aortic blood pressure.

CADs that are operated in co- or counterpulsation modalities requires timing in synchrony with the native heart. A need exists to provide a timing algorithm and device(s) that can provide such synchrony.

BRIEF DESCRIPTION OF THE DRAWINGS

The accompanying drawings illustrate several embodiments and, together with the description, serve to explain the disclosed principles. One skilled in the relevant art will understand, however, that embodiments can be practiced without all of the specific details of the illustrated examples. Likewise, one skilled in the relevant art will also understand that the technology may include well-known structures or functions not specifically illustrated to avoid unnecessarily obscuring the relevant descriptions of the various examples. In the drawings.

DETAILED DESCRIPTION

Figure 1:
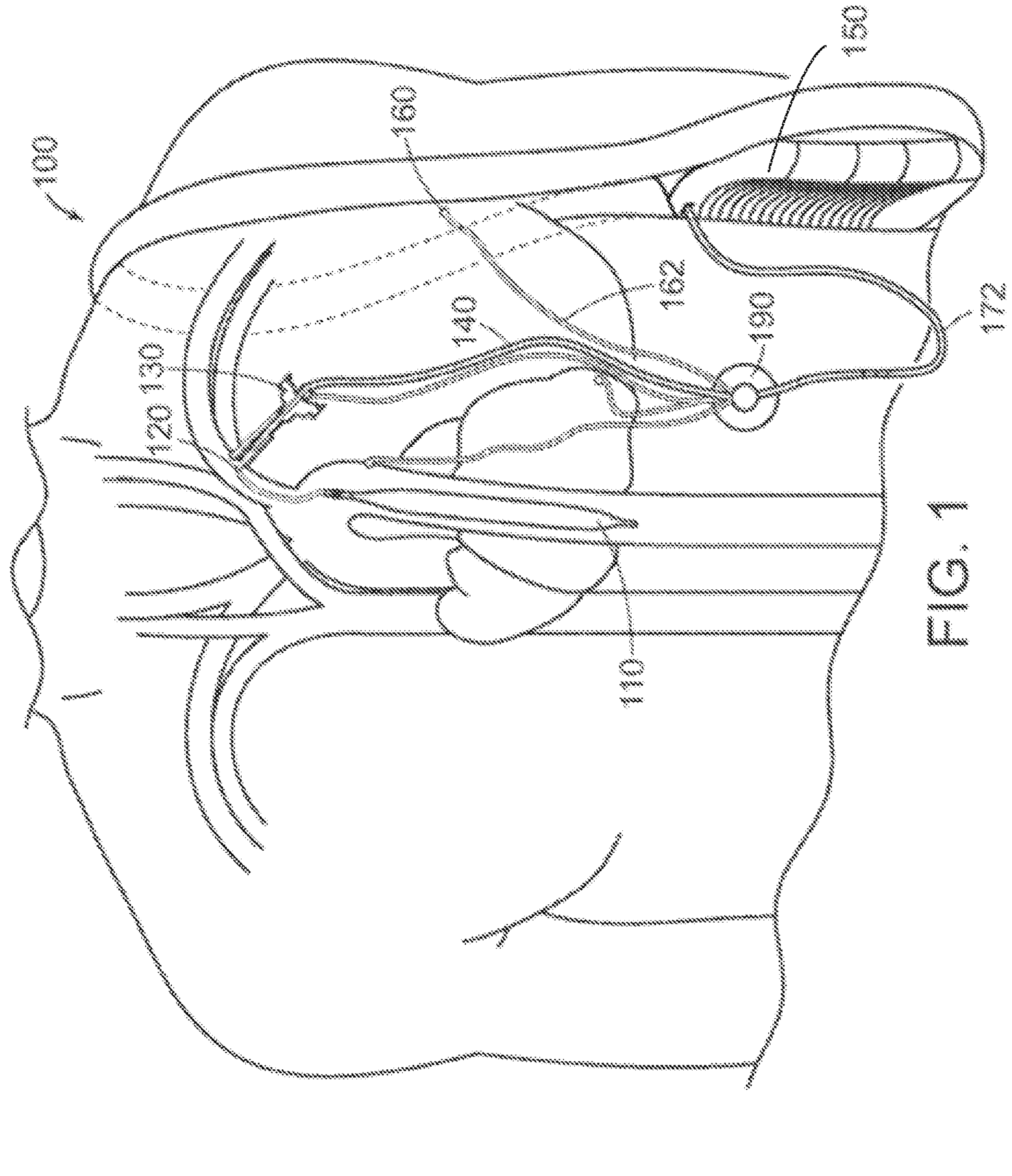
FIG. 1 illustrates an exemplary intravascular circulatory support system implanted within a patient's vasculature and configured in accordance with embodiments of the present technology.

CADs that are operated in co- or counterpulsation modalities may process electrocardiogram (ECG) signals for efficient and optimum operation. One of the most important parts of ECG signal processing and CAD operation is interpretation of QRS complex and obtaining its characteristics. The QRS complex is a name for the combination of three of the graphical deflections seen on a typical ECG. In adults, the QRS complex normally lasts 0.06-0.10 seconds; in children and during physical activity, it may be shorter. The three deflections include the Q-wave, the R-wave, and the S-wave. These waves occur in rapid succession, may not all appear in all leads, and reflect a single event and thus are usually considered together. In a typical ECG signal, a Q-wave is any downward deflection immediately following a P-wave, an R-wave follows as an upward deflection, and the S-wave is any downward deflection after the Q-wave. A T-wave follows the S-wave, and in some cases, an additional U-wave follows the T-wave. In some ECG signals, the Q-wave is an upward deflection, the R-wave follows as a downward deflection, and the S-wave is an upward deflection.

The R-wave is one of the most important sections of this complex, which has an essential role in diagnosis of heart rhythm irregularities and also in determining heart rate variability (HRV). In respect of counterpulsation CADs (e.g., counterpulsation devices and CADs operated in counterpulsation modalities), and copulsation CADs (e.g., CADs operated in copulsation modalities), the R-wave may be used as a key marker to determine/detect systole and/or diastole. In respect of IABPs, the R-wave may precede the ventricular contraction by 80-150 ms and is a key marker to initiate rapid deflation of the balloon such that the balloon is not obstructive in the aorta when the ventricle starts ejecting blood. Traditional systems for detecting the QRS complex include differentiation methods, digital filters, neural networks, filter banks, hidden Markov models, genetic algorithm, and maximum a posterior (MAP) estimator. These methods are highly sensitive to noise and generally cause errors in detecting the correct timing of R-waves in ECG signals. As a result, conventional systems and methods for intra-aortic balloon pumps suffer from an inability to predictively time the inflation and/or deflation of the balloon pump. Similar problems exist for other CADs, including those operating in co- and counterpulsation modalities.

In view of the shortcomings of conventional approaches to accurately detect the occurrence and timing of R-waves, there is a practical need in the technology of R-wave detection for that is more accurate, reliable, efficient, and that improves the safety and efficacy of CADs, including CADS operating in co- or counterpulsation modalities.

Hereinafter, the technology described herein will be described in connection with IABPs and counterpulsation. While the disclosed technology may be particularly useful for counterpulsation, it may have application to various other technologies and devices including other CADs (e.g., CADs for operation in copulsation modalities, CADs for operation in counterpulsation modalities), pacemakers, heart monitors, defibrillators, heartrate monitors, smart watches, athletic accessories, etc. References to counterpulsation shall include reference to copulsation and other therapy modalities for CADs and the devices identified in this paragraph.

Several embodiments are discussed below in more detail in reference to the figures. Other embodiments in addition to those described herein are within the scope of the present technology. Moreover, a person of ordinary skill in the art will understand that embodiments of the present technology may have configurations, components, and/or procedures in addition to those shown or described herein and that these and other embodiments may be implemented without several of the configurations, components, and/or procedures shown or described herein without deviating from the present technology. Reference throughout this description to "one embodiment," "an embodiment," "one or more embodiments," an "nth embodiment," or "some embodiments" means that a particular feature, support structure or characteristic described in connection with the embodiment is included in at least one embodiment of the present disclosure. Thus, use of such terminology is not necessarily referring to the same embodiment. For example, it is expressly contemplated that the features described herein may be combined in any suitable manner in one or more embodiments.

Intravascular Circulatory Support System Components

FIG. 1 illustrates an exemplary intravascular circulatory support system 100 implanted within a patient's vasculature. System 100 may include an intra-aortic balloon pump 110 implantable in an aorta of a patient suffering from heart failure. System 100 may further include a first driveline 120 (also referred to as an "internal driveline"), an arterial interface device or stopper device 130, a second driveline 140, a skin or patient interface device 190, tube 172, a drive unit 150, and sensors 160. When implanted, system 100 may provide counterpulsation therapy to a patient suffering from heart failure. In some embodiments, the intravascular circulatory support system 100 may have certain features generally similar to those described in U.S. patent application Ser. No. 16/876,110, the disclosure of which is incorporated herein by reference in its entirety.

Balloon pump 110 may be an expandable member, a balloon or other element that may change size and/or shape in response to being filled with a gas or liquid. For example, in some embodiments the balloon pump 110 is a balloon composed of a biocompatible, non-thrombogenic elastomeric material (e.g., Biospan®-S). Balloon pump 110 may also be made of other suitable materials. Balloon pump 110 may be transitioned between at least a first state in which it is generally deflated and a second state in which it is generally inflated. The balloon pump 110 may have a first volume when in the first (e.g., deflated) state and a second volume that is greater than the first volume when in the second (e.g., inflated) state. Accordingly, the balloon pump 110 may provide counterpulsation therapy by repeatedly transitioning between the first state and the second state. To transition the balloon pump 110 between the first state and the second state, the drive unit 150 may direct a fluid (gas or liquid, e.g., air) into an internal volume of the balloon pump 110 via the first driveline 120, the second driveline 140, and tube 172. Balloon pump 110 may be sized and/or shaped to reduce and/or prevent blocking of arteries branching from the aorta, such as the renal arteries. In some embodiments, the balloon pump 110 includes an expandable end effector other than or in addition to a balloon. In some embodiments, the balloon pump 110 may have certain features generally similar to those described in U.S. Pat. Nos. 8,066,628, 8,323,174, and 8,326,421 and U.S. patent application Ser. Nos. 17/944,130, 17/944,127, and 17/944,125, the disclosures of which are incorporated herein by reference in their entireties.

The first driveline 120 may be an elongated structure having a lumen extending therethrough for delivering inflation gases to balloon pump 110. The first driveline 120 may be able to be positioned at least partially within the patient's vasculature (e.g., between the aorta and an axillary or subclavian artery). After the system 100 is implanted, the first driveline 120 may have a first end portion (e.g., a distal end portion) coupled to the balloon pump 110 and positioned within the patient's vasculature (e.g., within a descending aorta) and a second end portion (e.g., a proximal end portion) coupled to the second driveline 140 and positioned external to the patient's vasculature. The first driveline 120 may exit the patient's vasculature at an arteriotomy in, for example, an axillary artery, a subclavian artery, or another suitable blood vessel.

The second driveline 140 may also be an elongated structure having a lumen extending therethrough. The second driveline 140 may be able to be positioned at least partially subcutaneously but external to the patient's vasculature. After the system 100 is implanted, the second driveline 140 may have a first end portion (e.g., a distal end portion) coupled to the first driveline 120 and a second end portion (e.g., a proximal end portion) coupled to the patient interface device 190. The first driveline 120 and the second driveline 140 may be made of the same or different materials, and may have the same or different dimensions (e.g., length, outer diameter, inner diameter, etc.). In some embodiments, the second driveline 140 may include an absorptive feature for reducing longitudinal strain that could otherwise be transferred to the first driveline 120 when the patient moves. For example, in some embodiments the absorptive feature is a curved region (e.g., an "S" shaped or other serpentine curve) that can compress in response longitudinal forces, thereby reducing and/or preventing the longitudinal forces from being transferred to the intravascular portions of the system 100 (e.g., the first driveline 120 and/or the balloon pump 110).

The first driveline 120 may be coupled to the second driveline 140 using any suitable technique. In some embodiments, the first driveline 120 is inserted at least partially into the second driveline 140 (or vice versa) and secured thereto using a compression ring. In some embodiments, the first driveline 120 is sutured, glued, stitched, or otherwise secured to the second driveline 140. In some embodiments, the first driveline 120 is attached to the second driveline 140 via a combination of the foregoing techniques and/or via other suitable attachment techniques. Regardless of the connection mechanism, when the first driveline 120 is coupled to the second driveline 140, the lumen of the first driveline 120 may be fluidly connected to the lumen of the second driveline 140 such that gases that flow through the lumen of the second driveline 140 also flow through the lumen of the first driveline 120. Although described as first and second drivelines, in some embodiments the first driveline 120 and the second driveline 140 may be a single, integral component (i.e., a single driveline).

As noted above, the first driveline 120 may be coupled to the balloon pump 110 to deliver inflation gases thereto. For example, the first end portion of the first driveline 120 may be connected to the balloon pump 110 such that the lumen extending through the first driveline 120 is in fluid communication with an interior of the balloon pump 110. Accordingly, gas flowing through the lumen of the first driveline 120 towards the balloon pump 110 may flow into the balloon pump 110, causing the balloon pump 110 to transition from the first state to the second state (e.g., causing the balloon pump 110 to inflate). The first driveline 120 may also receive gas from the balloon pump 110 as the balloon pump 110 transitions between the second state and the first state (e.g., as the balloon pump 110 deflates).

The arterial interface device or stopper device 130 may provide long-term (e.g., greater than about 3 months, greater than about 6 months, greater than about 12 months, etc.) hemostasis at an arteriotomy where the first driveline 120 exits the vasculature (e.g., at the subclavian or axillary artery). The stopper device 130 may include a plurality of anchoring elements that may be used to secure the stopper device 130 in a desired orientation or position. In some embodiments, the stopper device 130 may include certain features generally similar to those described in U.S. Pat. No. 7,892,162, the disclosure of which is incorporated herein by reference in its entirety. For example, the stopper device 130 may include a suture ring (e.g., a polyester velour patch sutured to the artery to provide mechanical support), a graft (e.g., a polyester textile defining a lumen and sutured to the suture ring and artery to provider arterial access), and a stopper element (e.g., a silicone plug inserted into the lumen of the graft to provide hemostasis having a lumen that receives the first driveline 120).

The patient interface device 190 may be a transcutaneous device that enables the external drive unit 150 to drive operation of the implanted balloon pump 110. For example, in some embodiments the patient interface device 190 provides a stable and/or secure exit site for the second driveline 140, enabling connection of the second driveline 140 directly to the drive unit 150. In other embodiments, the second driveline 140 may be coupled to an internal facing portion of the patient interface device 190, and the drive unit 150 may be coupled to an external facing portion of the patient interface device 190 via tube 172. Tube 172 may be a tube, hose, and/or other conduit having an elongated structure having a lumen extending therethrough. For example tube 172 may comprise an air tube having a lumen extending therethrough and one or more electrical conduits for serial communication between patient interface device 190 and drive unit 150. In such embodiments, the patient interface device 190 may direct gases received from the drive unit 150 (e.g., via the tube 172) to the second driveline 140 for delivery to the expandable member 110. In some embodiments, the patient interface device 190 may have certain features generally similar to those described in U.S. Pat. No. 10,137,230, the disclosure of which is incorporated herein by reference in its entirety.

The drive unit 150 may generate gas flow into and out of the balloon pump 110 via the first driveline 120, the second driveline 140, and tube 172. For example, the drive unit 150 may generate a positive pressure to accelerate gases into the balloon pump 110 via the first driveline 120, the second driveline 140 and tube 172, thereby inflating the balloon pump 110. The drive unit 150 may also induce a negative pressure to withdraw gases from the balloon pump 110 via the first driveline 120, the second driveline 140, and tube 172, thereby deflating the balloon pump 110. The drive unit 150 may induce gas flow into and out of the balloon pump 110 through a number of different mechanisms. For example, the drive unit 150 may utilize a bellows, a blower, a compressor, an accelerator, or other similar features to direct gas flow into and out of the balloon pump 110. In some embodiments, the drive unit 150 may control the volume of air being pushed into the balloon pump 110 to avoid overinflating the balloon pump 110. For example, in an embodiment utilizing a bellows to generate air flow, the volume of airflow generated by the bellows (e.g., the volume of the bellows) may be matched to an interior volume of the balloon pump 110. In some embodiments, the drive unit 150 uses ambient air from the environment surrounding the drive unit 150 (e.g., "room air") to drive operation of the system 100. Without being bound by theory, using ambient air is expected to reduce the size, weight, and/or cost of the drive unit 150 relative to a drive unit that relies on an internal gas or fluid supply (e.g., helium tanks). For example, in some embodiments the drive unit 150 may weigh about 2.2 kg or less. Accordingly, in some embodiments the drive unit 150 may be portable/ambulatory. In other embodiments, the drive unit 150 may be operably coupled to or otherwise include a gas or fluid supply, such as helium tanks (not shown). The driveline 140 or tube 172 may be disconnected near the patient interface device 190 when the system 100 is not being actively used. In some embodiments the drive unit 150 may have certain features generally similar to those described in U.S. patent application Ser. No. 17/878,632, the disclosure of which is incorporated herein by reference in its entirety.

The sensors 160 may sense one or more physiological parameters related to the patient's native heart rhythm to synchronize operation of the system 100 with the cardiac cycle. In particular, one or more sensed physiological parameters may be used to automatically synchronize operation of the drive unit 150 with the patient's native heart beat to ensure the balloon pump 110 is being inflated and deflated at appropriate times during the cardiac cycle. In some embodiments, the sensors 160 may sense the one or more physiological parameters in real time. As illustrated in FIG. 1, the sensors 160 may be coupled to the patient interface device 190 via wires 162. Wires 162 may be intracardiac, subcutaneous, supercutaneous, or any combination of the foregoing. The patient interface device 190 may relay the sensor data (e.g., data received from the sensors 160) to the drive unit 150 via a wired or wireless connection. In other embodiments, the sensors 160 may be connected, via a wired or wireless connection, to the drive unit 150 and can transmit sensor data directly to the drive unit 150 without using the patient interface device 190. The sensors 160 may be implanted sensors, external sensors, or any combination of the foregoing. For example, in some embodiments, the sensors 160 may be implanted bipolar electrodes positioned at and/or proximate the heart or other appropriate tissue to determine, for example, when the left ventricle is contracting or relaxing. Sensors 160 may deliver to the drive unit 150, one or more of the following: the heart's electrical signal(s) (e.g., signals which may processed and displayed on a monitor or printer as an ECG signal), pressure information associated with the pressure proximate the balloon pump 110 (e.g., proximate the proximal end of the balloon pump 100), ambient noise information (e.g., noise associated with the pectoral muscle, electronic noise from the system 100 or from other devices (not depicted) associated with or in proximity to the patient, etc.), noises made by the heart during a cardiac cycle (e.g., information that may be processed and displayed on a monitor or printer as an phonocardiograph signal), other pressure signals, etc. In some embodiments, sensors 160 are electronic sound transducers, pressure transducers, piezoelectric transducers or other transducers or sensors suitable for making physiological parameter measurements. Although FIG. 1 depicts three sensors 160, system 100 may incorporate less or more than three sensors 160 depending on the nature of what is being sensed in any particular embodiment.

System 100 may provide chronic support of heart function and blood flow, while still allowing the patient to remain ambulatory. Typical ventricular assist devices require femoral access for the driveline and/or connection to large, stationary external control units, and therefore confine the patient to a hospital bed in supine position for the duration of therapy. In contrast, the system 100 may provide axillary/subclavian access and therefore allow the patient to move about relatively unencumbered. Moreover, the therapy level provided by the system 100 may be adjusted to match patient need. For example, the volume displacement and support ratio (e.g., 1:1, 1:2, 1:3 support) provided by the balloon pump 110 may be adjusted to vary the support provided. Without being bound by theory, gradually reducing the volume displacement over time may result in a controlled loading of the heart which in some instances may be beneficial for cardiac recovery. Furthermore, unlike conventional circulatory support systems, the system 100 may be turned off to, for example, assess the ability of the patient to handle cardiac demand without support before removing the system 100, or for another suitable reason. In some embodiments, for example, the balloon pump 110 is designed to remain in the aorta in a deflated condition for a relatively prolonged duration (e.g., for 23 hours in a single day). This is in direct contrast to conventional devices, which often must be removed if turned off for more than about 15 minutes because reactivation could result in a shower of emboli that formed when in the inactive state.

Cardiac Cycle Signals

Figure 2:
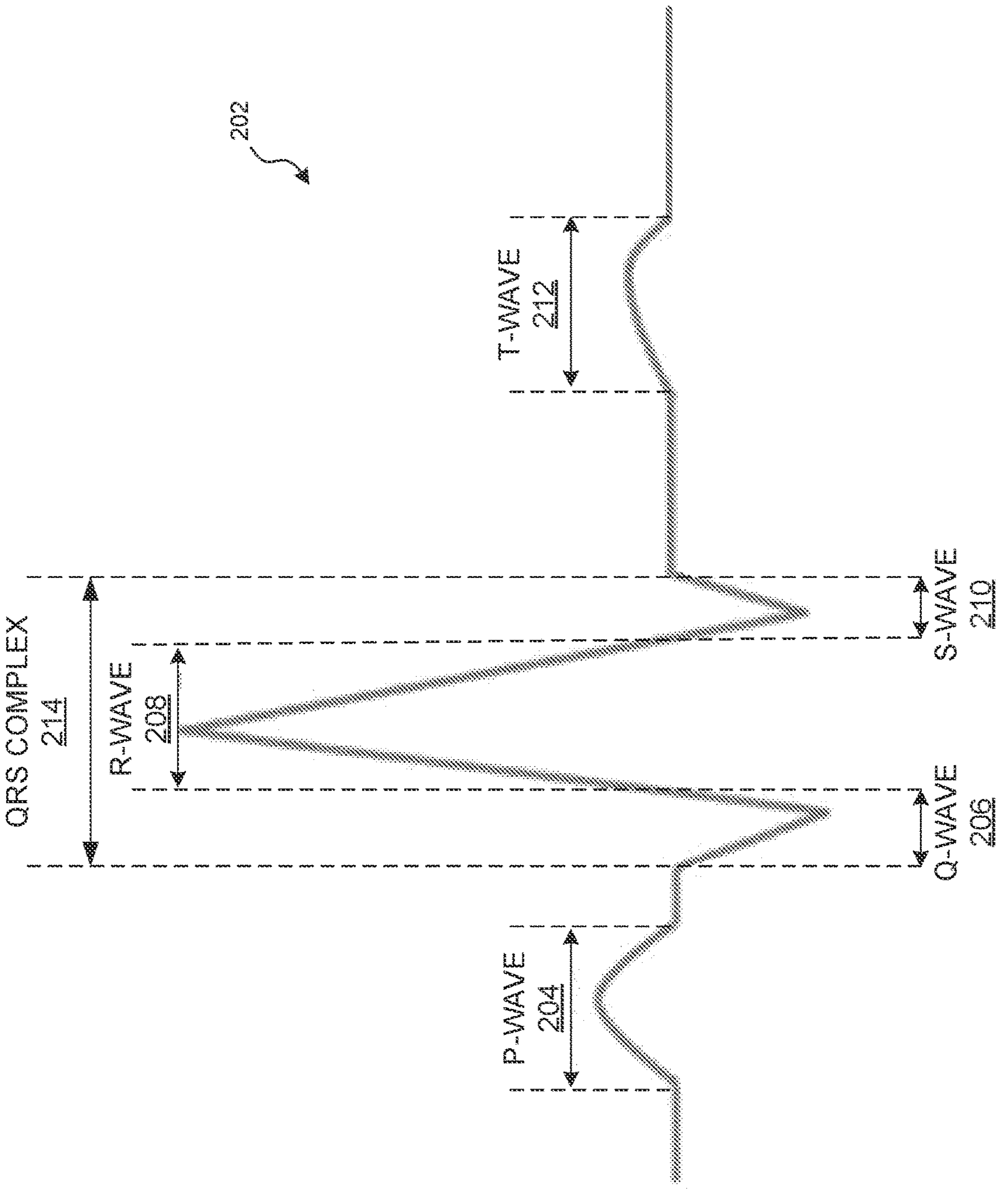
FIG. 2 illustrates an exemplary QRS complex in an electrocardiogram (ECG) signal in accordance with some embodiments of the present technology.

FIG. 2 illustrates an exemplary ECG signal 202. The ECG signal 202 may be sensed by sensors 160. ECG signal 202 may include P-wave 204, Q-wave 206, R-wave 208, S-wave 210 and T-wave 212. The Q-wave 206, R-wave 208 and S-wave 210 may constitute a QRS complex 214.

Figure 3:
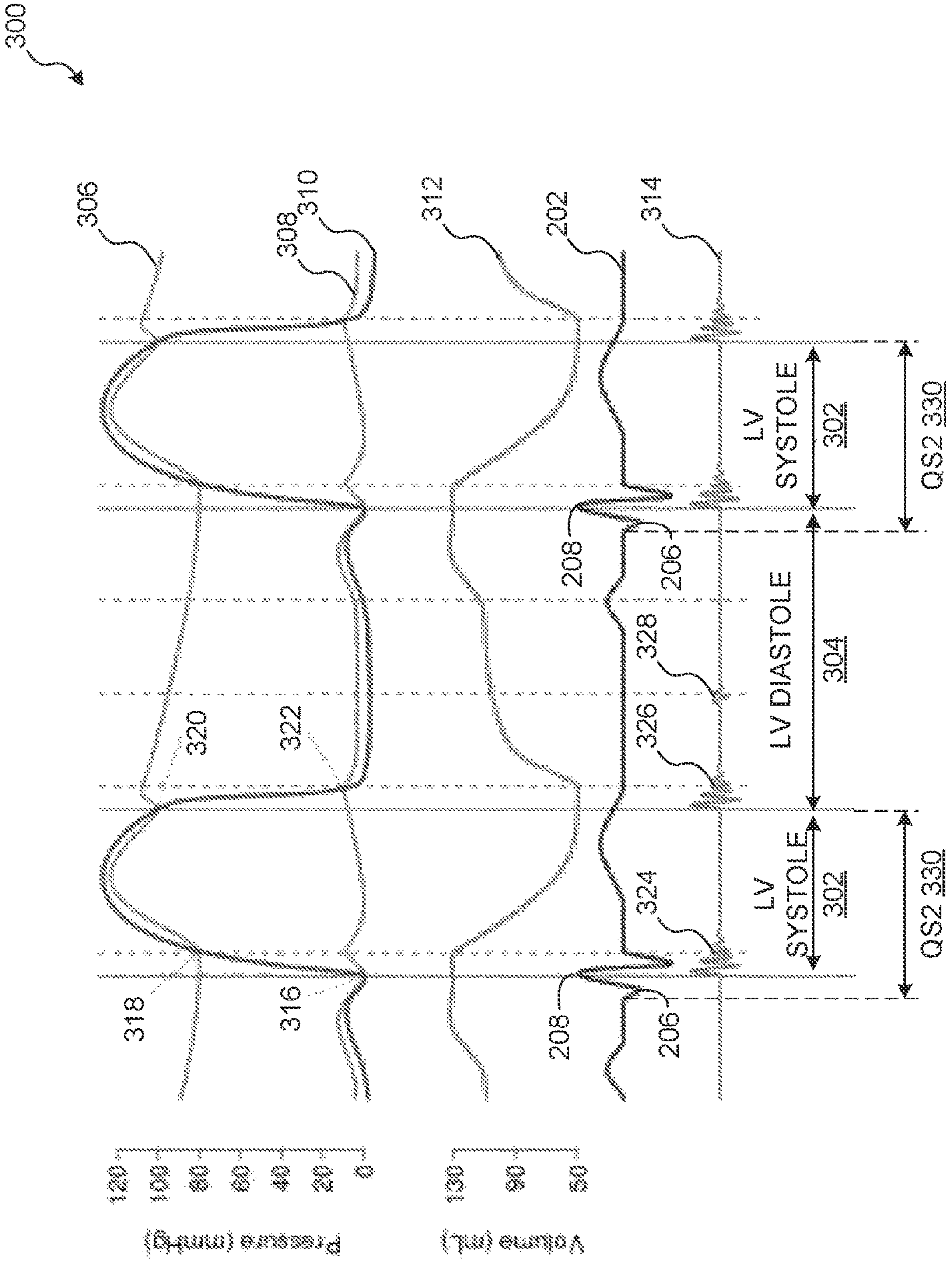
FIG. 3 illustrates an exemplary Wiggers Diagram in accordance with some embodiments of the present technology.

FIG. 3 illustrates an exemplary Wiggers Diagram 300 of an exemplary cardiac cycle. The x-axis of the diagram plots time and is subdivided into the cardiac phases (left ventricular systole 302 and left ventricular diastole 304), while the y-axis of the diagram plots blood pressures (aortic pressure 306, atrial pressure 308, and ventricular pressure 310), ventricular volume 312, the ECG signal 202, and the phonocardiogram signal 314. The Wiggers Diagram 300 also illustrates, among other things, cardiac timing for the closing of the mitral valve 316, the opening of the aortic valve 318, the closing of the aortic valve 320 (i.e., the dicrotic notch), and the opening of the mitral valve 322, in addition to the S1 heart sounds 324, the S2 heart sounds 326 and the S3 heart sounds 328. The R-wave 208 represents the onset of left ventricular systole 302 and the dicrotic notch 320 or the S2 heart sound 326 represents the onset of left ventricular diastole 304.

Drive Unit System

Figure 4:
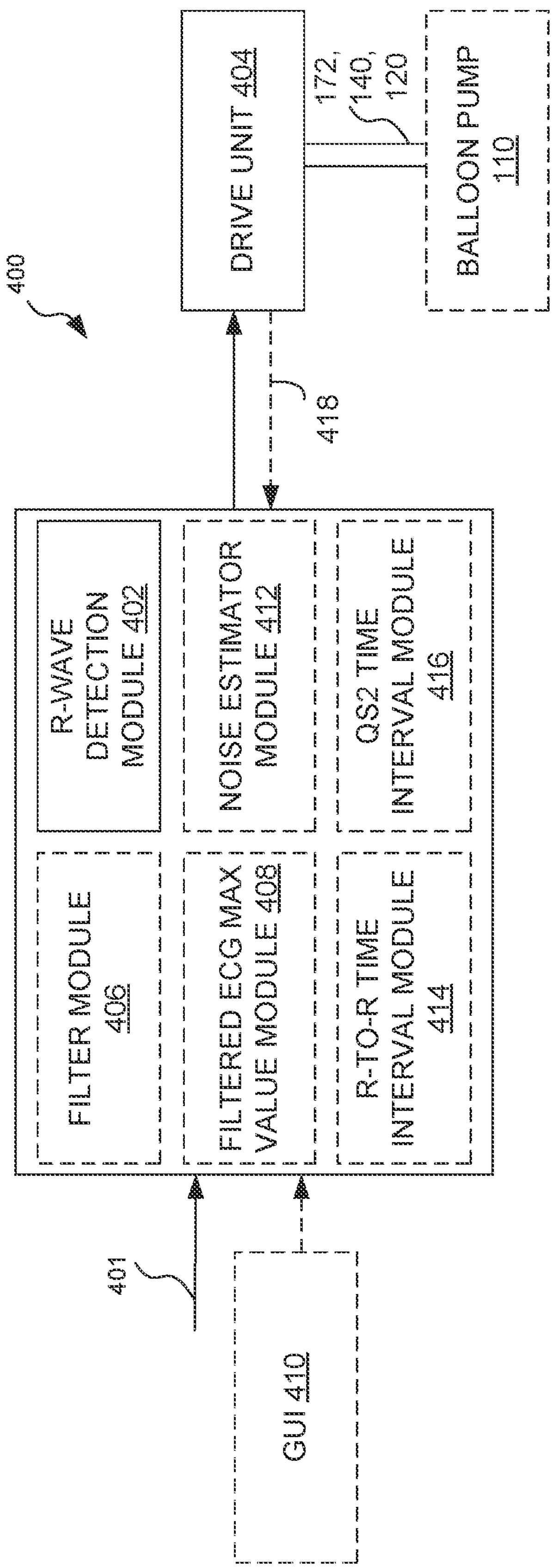
FIG. 4 illustrates an exemplary schematic of a drive unit system in accordance with some embodiments of the present technology.

FIG. 4 illustrates an exemplary schematic of a drive unit system 400 in accordance with some embodiments of the present technology. Drive unit system 400 may include R-wave detection module 402 and drive unit 404. R-wave detection module 402 may detect one or more R-waves associated with a received ECG signal (as measured by sensors 160 and received as sensor data 401). When in operation, drive unit 404 may be coupled to an intra-aortic balloon pump 110 via tube 172, second driveline 140 and first driveline 120, the balloon pump 110 having been placed in the proximity of a patient's heart as generally depicted in FIG. 1. The patient may be a human or other animal. In some embodiments, the drive unit system 400 may include balloon pump 110. The drive unit 404 may inflate and deflate the balloon pump 110 based on a detection of an R-wave. As such, the balloon pump 110 may perform counterpulsation.

Filtered ECG Signal

In some embodiments, drive unit system 400 includes filter module 406. Filter module 406 may convert a received ECG signal into a filtered ECG signal that accentuates the R-waves contained in the ECG signal and/or that attenuates all or some of the other frequencies and waves that are not part of the R-waves. For example, filter module 406 may filter out all frequencies within an ECG signal other than frequencies anticipated to define or otherwise contribute to R-waves 208. Such anticipated frequencies may be determined empirically and used as settings (e.g., by a clinician). In some embodiments, filter module 406 filters out frequencies other than those in the 7.8125 Hz to 15.625 Hz band. In other embodiments, filter module 406 filters out frequencies other than those in the 15.625 Hz to 31.25 Hz band. In yet other embodiments, filter module 406 filters out frequencies other than those in the 7.8125 Hz to 31.25 Hz band. In some embodiments, the output of filter module approximates an absolute value of the derivative of a smoothed version of the received ECG signal. In some embodiments, filter module 406 may be implemented as a bandpass filter, a weighting filter or a wavelet filter.

Figure 5A:
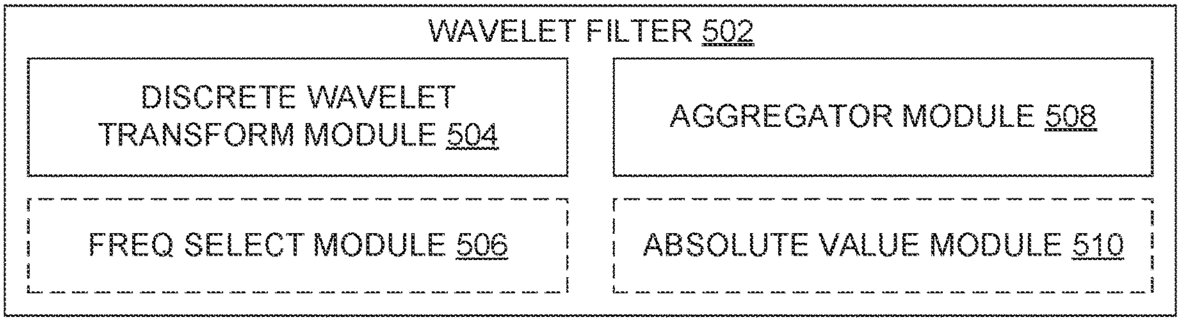
FIG. 5A illustrates an exemplary schematic of a wavelet filter in accordance with some embodiments of the present technology.
Figure 5B:
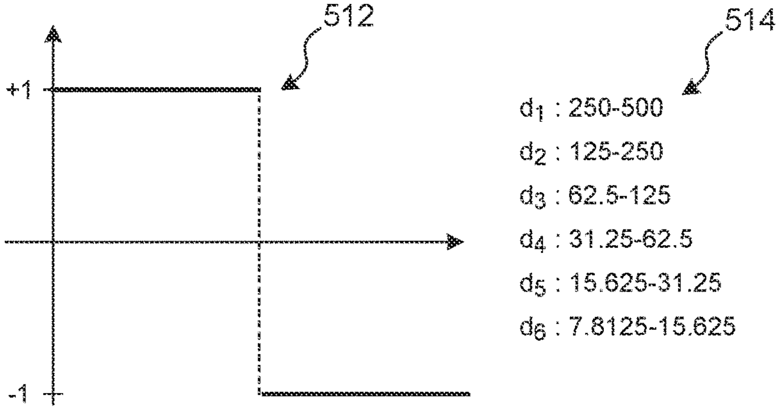
FIG. 5B illustrates an exemplary mother Haar wavelet function in accordance with some embodiments of the present technology.
Figure 5C:
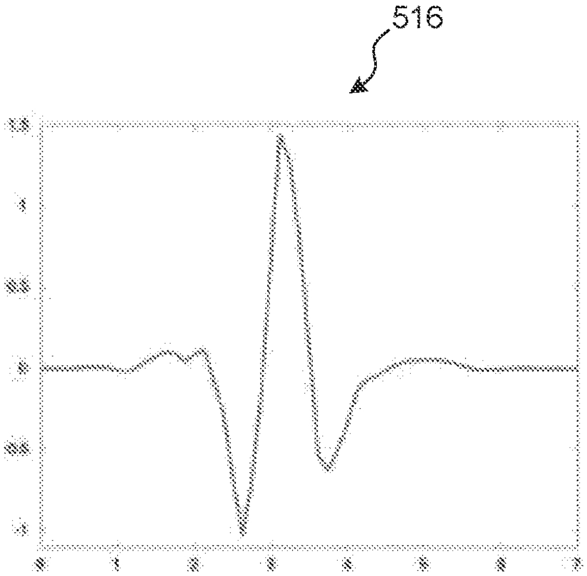
FIG. 5C illustrates an exemplary mother symlet4 wavelet function in accordance with some embodiments of the present technology.
Figure 5D:
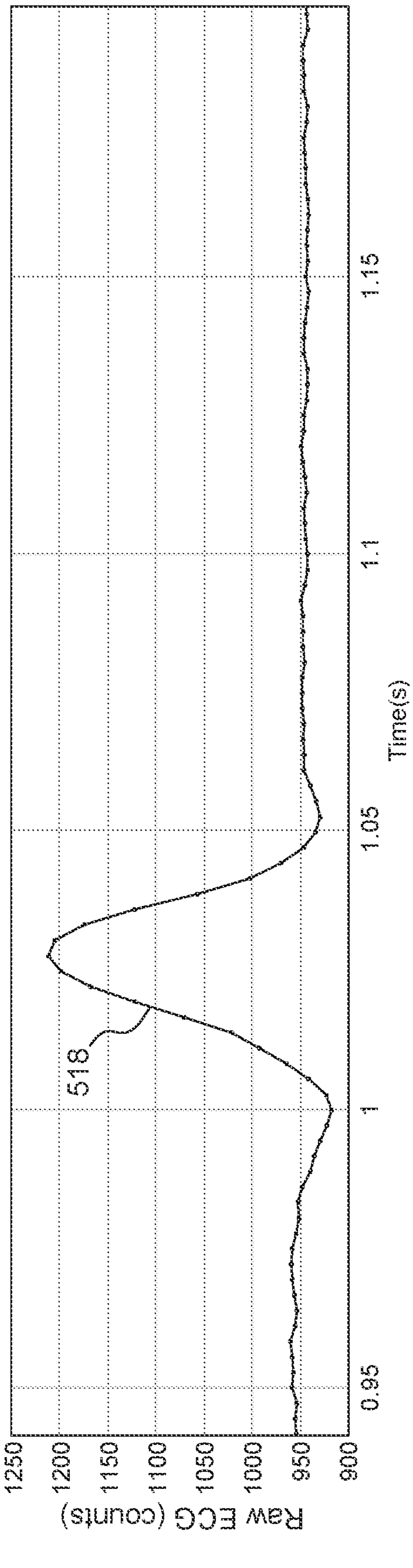
FIG. 5D illustrates an exemplary ECG signal received by the drive unit system of FIG. 4 in accordance with some embodiments of the present technology.
Figure 5E:
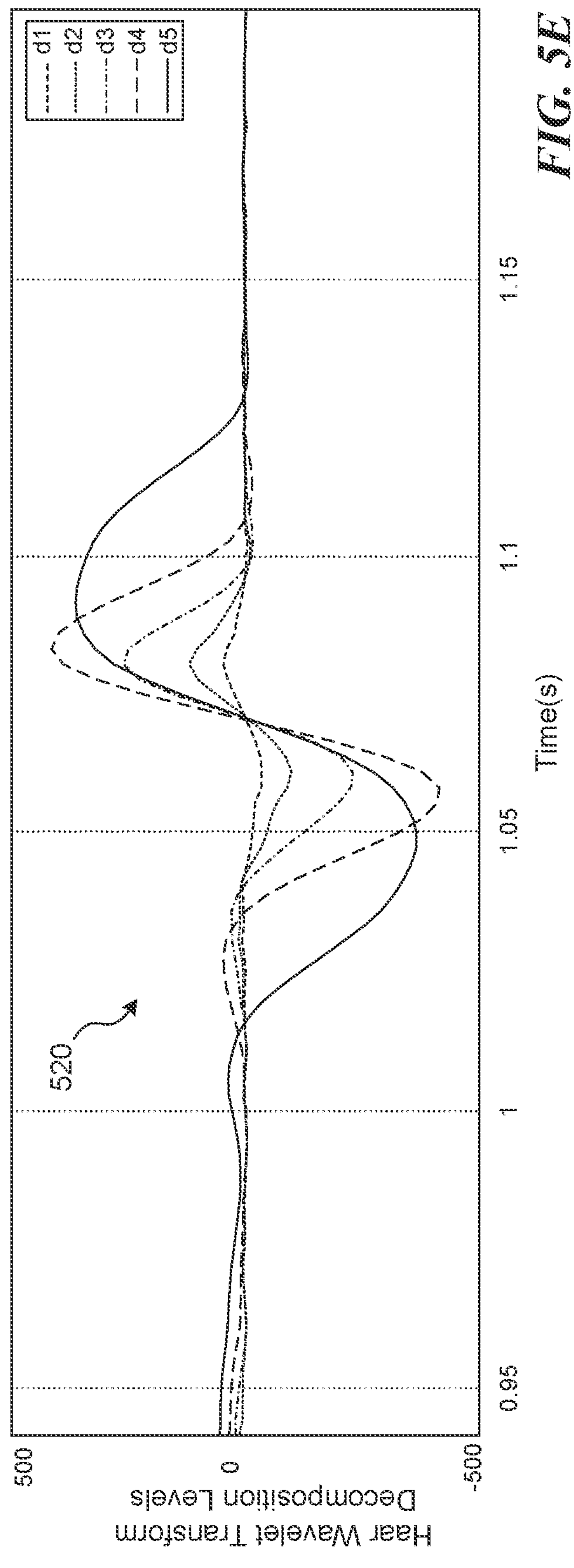
FIG. 5E illustrates a plot of an exemplary plurality of discrete frequency signals obtained by decomposing the ECG signal of FIG. 5D using the Haar mother wavelet function of FIG. 5B in accordance with some embodiments of the present technology.
Figure 5F:
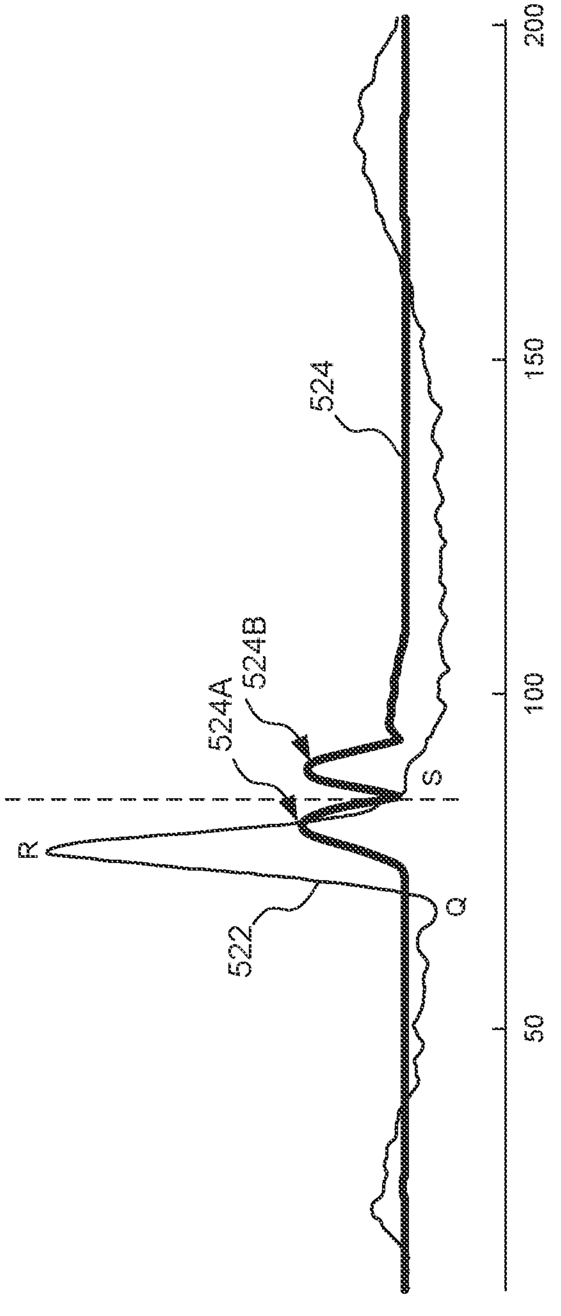
FIG. 5F illustrates a plot of an exemplary filtered ECG signal and its corresponding ECG signal in accordance with some embodiments of the present technology.

FIG. 5A illustrates a schematic of wavelet filter 502. FIG. 5B illustrates an exemplary mother Haar wavelet function 512 that may be employed by wavelet filter 502. FIG. C illustrates an exemplary mother symlet4 wavelet function 516 that may be employed by wavelet filter 502. FIG. 5D illustrates an exemplary ECG signal that may be received by drive unit system 400 and FIG. 5E illustrates a plot 520 of exemplary plurality of discrete frequency signals obtained by wavelet filter 502 decomposing ECG signal 518 using a Haar wavelet function (e.g., function 512). FIG. 5F illustrates a plot of an exemplary filtered ECG signal 524 and its corresponding ECG signal 522.

With reference to FIGS. 5A-5F, filter module 406 may be implemented as wavelet filter 502. Wavelet filter 502 may include a discrete wavelet transform module 504, a frequency selector module 506, an aggregator module 508 and an absolute value module 510. Discrete wavelet transformation module 504 may decompose at least a portion of a received ECG signal (e.g., ECG signal 518) into a plurality of discrete frequency signals (e.g., discrete frequency signals depicted in plot 520 corresponding to coefficients created from a decomposition), each associated with a different frequency band using, for example, one or more wavelet transformation functions such as a mother Haar wavelet (Psi) function 512 or a mother Symlet 4 wavelet (Psi) function 516.

The decomposition may be a multistep decomposition conducted at a plurality of levels, that generates wavelet approximation (a) and detail (d) coefficients at each level. For example and with reference to FIG. 5B, the detail (d) coefficients 514 associated with level 1 (d1) may be in the 250-500 Hz sub-band; the detail coefficients 514 associated with level 2 (d2) may be associated with the 125-250 Hz sub-band; the detail coefficients 514 associated with level 3 (d3) may be associated with the 62.5-125 Hz sub-band; the detail coefficients 514 associated with level 4 (d4) may be associated with the 31.25-62.5 Hz sub-band; the detail coefficients 514 associated with level 5 (d5) may be associated with the 15.625-31.25 Hz sub-band; and the detail coefficients 514 associated with level 6 (d6) may be associated with the 7.8125-15.625 Hz sub-band. In some embodiments, the decomposition may only generate those discrete frequency signals associated with frequencies or frequency bands anticipated to define or otherwise contribute to R-waves.

Aggregator module 508 may aggregate one or more of the decomposed discrete frequency signals. In some embodiments, a frequency selector module 506 may be configured to identify the frequencies or frequency bands that are anticipated to define or otherwise contribute to R-waves (e.g., frequencies in the 7.8125 Hz to 15.625 Hz and 15.625 Hz to 31.25 Hz bands, associated with the d6 and d5 coefficients). For example, in embodiments where a plurality of discrete frequency signals are generated, frequency selector module 506 may identify and select the one or more discrete frequency signals that may be aggregated by aggregator module 508. In other embodiments, the frequency selector module 506 may tune the wavelet filter 502 to generate only those discrete frequency signals associated with frequencies or frequency bands anticipated to define or otherwise contribute to R-waves, and aggregator module 508 may aggregate all of the generated decomposed discrete frequency signals. The aggregated signal may be the filtered ECG signal. In some embodiments, an absolute value module 510 may be employed to ensure that the filtered ECG signal is positive.

In some embodiments the wavelet filter 502 include an inverse discrete wavelet module that constructs or reconstructs a signal using one or more coefficients or decomposed discrete frequency signals. In such embodiments, the output of the inverse discrete wavelet module may be the filtered ECG signal. In some embodiments, an absolute value module 510 may be employed to ensure that the filtered ECG signal is positive.

With reference to FIG. 5F, an exemplary ECG signal 522 is depicted alongside its filtered ECG signal 524. Filtered ECG signal 524 may have two peaks, 524A and 524B, that corresponds to the rise from Q to R and the fall from R to S in the QRS complex 212. Peaks 524A and 524B may both be positive due to operation of the absolute value module 510. In embodiments where the absolute value module 510 is omitted, peak 524A and peak 524B will be of opposite sign and the shape of the filtered signal may resemble the shape of the decomposed signals in plot 520.

Figure 6A:
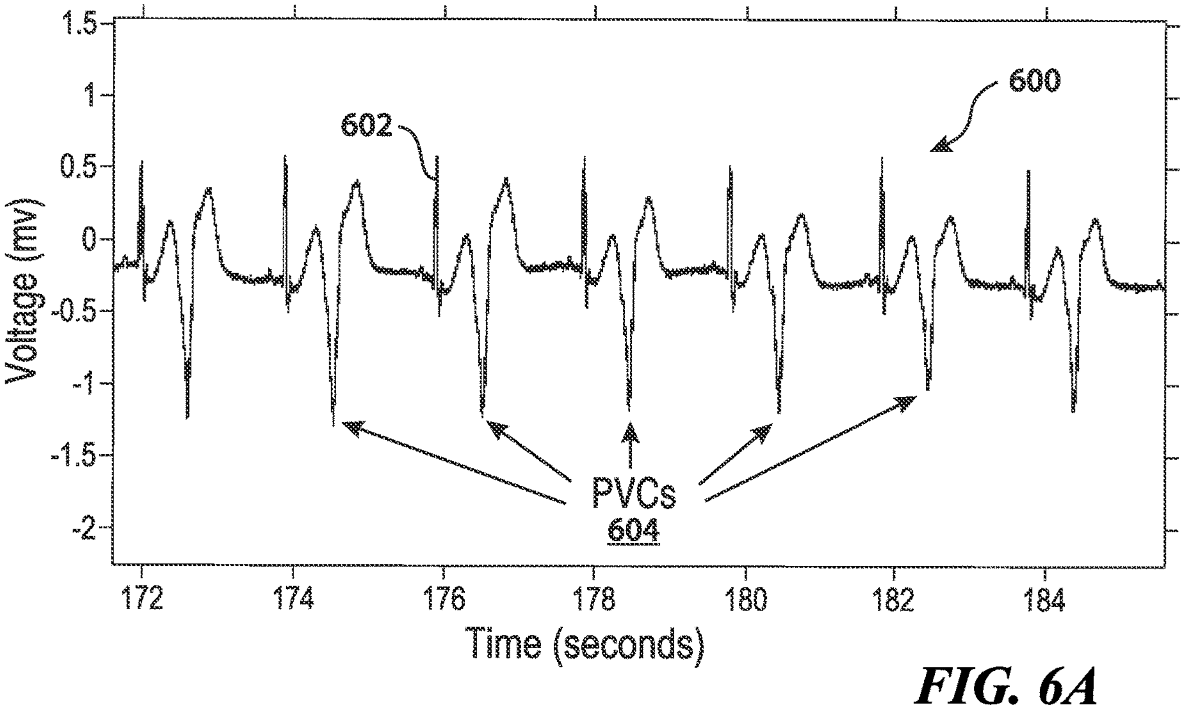
FIG. 6A illustrates a plot of an exemplary ECG signal containing PVCs in accordance with some embodiments of the present technology.
Figure 6B:
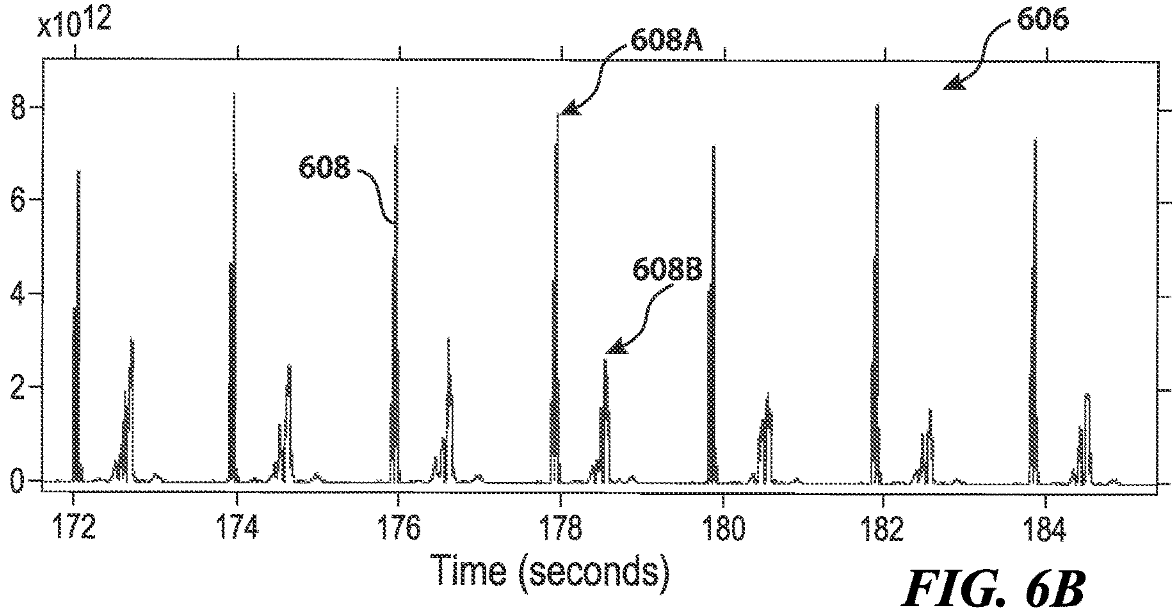
FIG. 6B illustrates a plot of an exemplary filtered ECG signal associated with the ECG signal of FIG. 6A in accordance with some embodiments of the present technology.

FIG. 6A illustrates a plot 600 of an exemplary ECG signal 602 containing multiple premature ventricular contractions (PVCs) 604 in accordance with some embodiments of the present technology. FIG. 6B illustrates a plot 606 of an exemplary filtered ECG signal 608 associated with the ECG signal 602 of FIG. 6A. The larger peaks 608A may be associated with the QRS complex 212 in the ECG signal 602 whereas the smaller peaks 608B may be associated with the PVCs 604.

R-Wave Detection

In some embodiments, R-wave detection module 402 may be configured to detect an R-wave associated with a received ECG signal by detecting a "crossing" of one or more R-wave detection threshold values by a filtered ECG signal. In some embodiments that do not employ an absolute value module 510, the embodiment may employ a positive and a negative R-wave detection threshold value and a "crossing" occurs when the current value of a filtered ECG signal (e.g., signal 524) crosses either R-wave detection threshold value (e.g., when the current value of a filtered ECG signal changes to become greater than the positive R-wave detection threshold value or changes to become less than the negative R-wave detection value). In embodiments where absolute value module 510 is employed, a filtered ECG signal may be positive and a "crossing" may occur when the current value of the filtered ECG signal changes to become greater than a R-wave detection threshold value.

Figure 7:
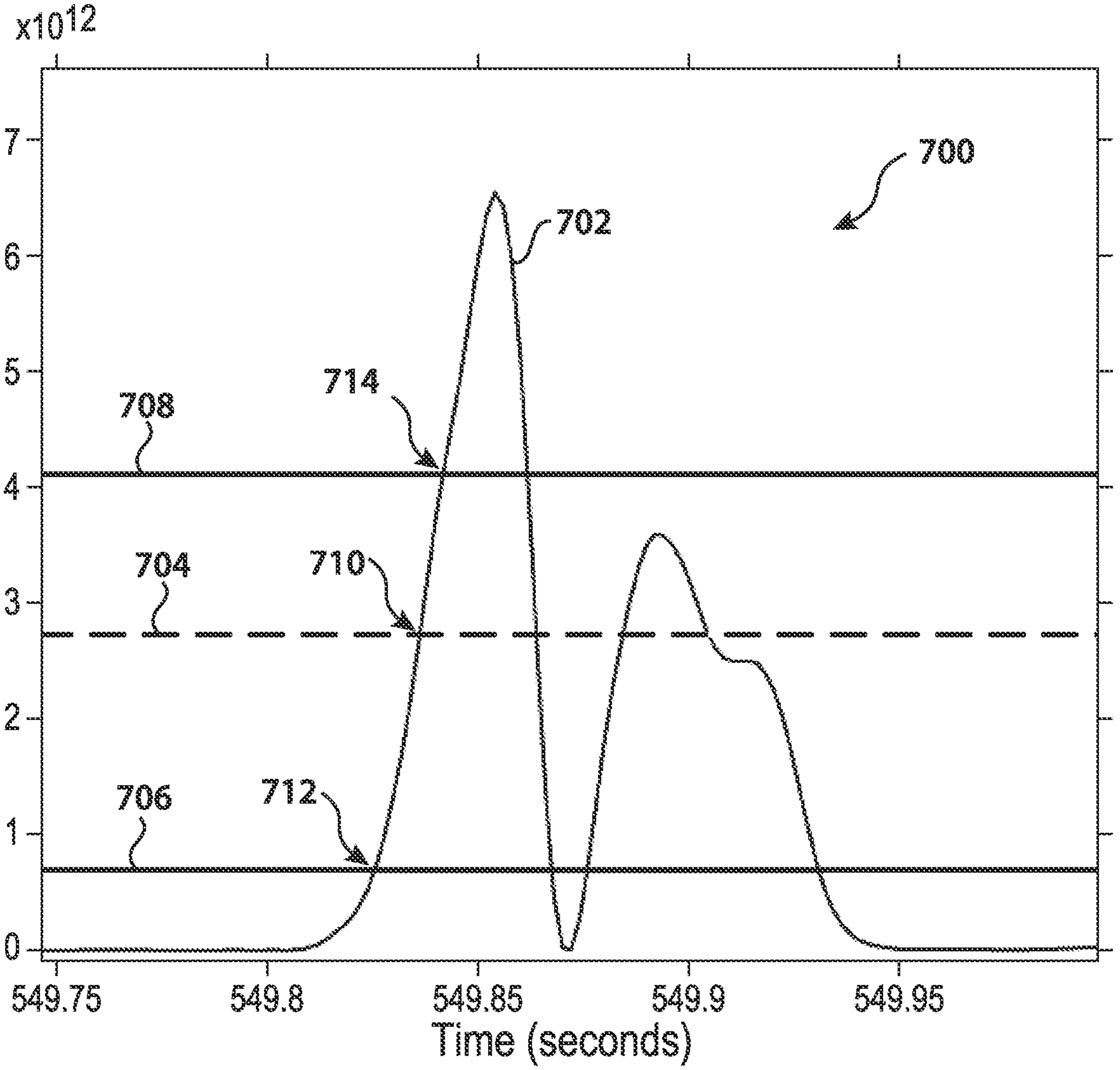
FIG. 7 illustrates a plot of a portion of an exemplary filtered ECG signal crossing a plurality of R-wave detection threshold values in accordance with some embodiments of the present technology.

FIG. 7 illustrates a plot 700 of a portion of an exemplary filtered ECG signal 702 highlighting a single QRS complex, a plurality of R-wave detection threshold values 704, 706, 708, and a plurality of crossing 710, 712, and 714 of filtered ECG signal 702 with respect to such R-wave detection threshold values 704, 706, 708. R-wave detection threshold values 704, 706, 708 may be any suitable value to support counterpulsation. In some embodiments, R-wave detection threshold values may be based on a predicted filtered ECG max value. In some embodiments, R-wave detection threshold values may represent a percentage of a predicted filtered ECG max value. For example, R-wave detection threshold value 704 may be about 40% of a predicted filtered ECG max value, R-wave detection threshold value 706 may be about 10% of a predicted filtered ECG max value, and R-wave detection threshold value 708 may be about 60% of a predicted filtered ECG max value.

In some embodiments, a single R-wave detection threshold value, e.g., nominal R-wave detection threshold value 704, is used to detect an R-wave. Nominal R-wave detection threshold value 704 may be set at about 40% of a predicted filtered ECG max value. In such embodiments, the crossing 710 of the single nominal R-wave detection threshold value 704 by the filtered ECG signal 702 may be considered a "nominal detection" of an R-wave and deflation of the balloon pump 101 may be based on such nominal detection. In particular, deflation may be based on a deflation trigger as discussed below. Upon detection of the crossing 710 (or nominal detection), driver unit 404 may promptly cause a deflation of balloon pump 101. In some embodiments, drive unit 404 may cause the balloon pump 110 to be at least 50% deflated in about 100-120 ms of the single crossing 710 and fully deflated in about 140-250 ms of the single crossing 710. Inflation can also be based on the same crossing 710 (as is described below).

Use of such a single nominal R-wave detection threshold value, e.g., nominal R-wave detection threshold value 704, and detection of a single crossing 710 (i.e., the nominal detection) may present challenges in supporting arrhythmic heart patterns such as atrial fibrillation (a-fib) and PVCs or in instances where the ECG is noisy (e.g., due to pectoral muscle activity or other noise interference). For example, and with reference to FIGS. 6A and 6B, if the single nominal R-wave detection threshold value 704 is set too high, it is possible to have a delayed detection of an R-wave or it is possible to "miss" or not detect R-waves (e.g., R-waves 608B associated with the PVCs 604) and ejection during the systole associated with such missed R-wave may consequently be resisted. In such an instance, it may be better to risk a false detection than risk missing the R-wave. Similarly, if the single nominal R-wave detection threshold value 704 is set too low such that there are false detections, e.g., caused by a noisy ECG signal (e.g., the noisy ECG signal 1002 in FIG. 10A, discussed below), then inflation might be triggered too early and ejection may also be resisted. In such an instance, it may be better to miss the R-wave than it is to have a false detection.

Two R-wave detection threshold values may also be used to detect an R-wave. For example, a first or relatively lower R-wave detection threshold value and a second or relatively higher R-wave detection threshold value may be employed, such values being relative to the single nominal R-wave detection threshold value. The crossing by the filtered ECG signal of the first or lower R-wave detection threshold value can be considered a "speculative detection" of an R-wave and consequently the first or lower R-wave detection threshold value may be considered a "speculative R-wave detection threshold value." Similarly, the crossing of the filtered ECG signal of the second or higher R-wave detection threshold value can be considered a "conservative detection" of an R-wave and consequently, the second or higher R-wave detection threshold value may be considered a "conservative R-wave detection threshold value."

In such embodiments where dual R-wave detection threshold values are used to make R-wave detections, the speculative detection may be associated with deflation only. Upon a speculative detection, driver unit 404 may promptly cause a deflation of balloon pump 101. In some embodiments, drive unit 404 may cause the balloon pump 110 to be at least 50% deflated in about 100-120 ms of the speculative detection and fully deflated in about 140-180 ms of the speculative detection. The conservative detection may be associated with inflation, as is described below.

For example, in FIG. 7, first or speculative R-wave detection threshold value 706 may be less than the single nominal R-wave detection threshold value 704. In the example of FIG. 7, the first R-wave detection threshold value 706 is about 10% of a predicted filtered ECG max value. A speculative detection may occur at crossing 712, i.e., when the filtered ECG signal 702 crosses first R-wave detection threshold value 706. As compared to single nominal R-wave detection threshold value 704 and for the same ECG signal, use of lower R-wave detection threshold value 706 may reduce the risk of not detecting (i.e., missing) the R-wave because, the speculative detection (i.e., crossing 712 as compared to crossing 710) is "earlier" (e.g., 10-25 ms earlier). This earlier-in-time speculative detection reduces the likelihood that the balloon pump 110 will stay inflated too long (i.e., during the early stages of LV systole 302).

Second or conservative R-wave detection threshold value 708 may be greater than the single nominal R-wave detection threshold value 704 so as to reduce the risk of a false detection of an R-wave. In the example of FIG. 7, the second R-wave detection threshold value 708 is about 60% of a predicted filtered ECG max value. A conservative detection may occur at crossing 714, i.e., when the filtered ECG signal 702 crosses second R-wave detection threshold value 708. As compared to single R-wave detection threshold value 704 and for the same ECG signal, use of higher (or greater in value) R-wave detection threshold value 708 may reduce the risk of a false detection of the R-wave and the conservative detection (i.e., crossing 714 as compared to crossing 710) may occur later in time. This later-in-time conservative detection reduces the chance of inflating early (e.g., during the later stages of LV systole).

Cumulatively, use of dual R-wave detection threshold values such as values 706 and 708 in lieu of a single nominal R-wave detection threshold value 704 means that in the vast majority of cases, R-waves may be detected due to a relatively lower speculative R-wave detection threshold value 704 and the balloon pump 110 will deflate in time. If, however, the relatively greater conservative R-wave threshold value 708 is not crossed, perhaps the only downside is that the cardiac cycle initiated by the undetected R-wave will not be supported with an inflated blood pump 110. An advantage with a dual threshold embodiment is that the detection of R wave may occur 10-20 ms earlier than the nominal detection, which enables earlier deflation of the balloon and minimizes its obstructive potential during ventricular ejection.

Figure 8A:
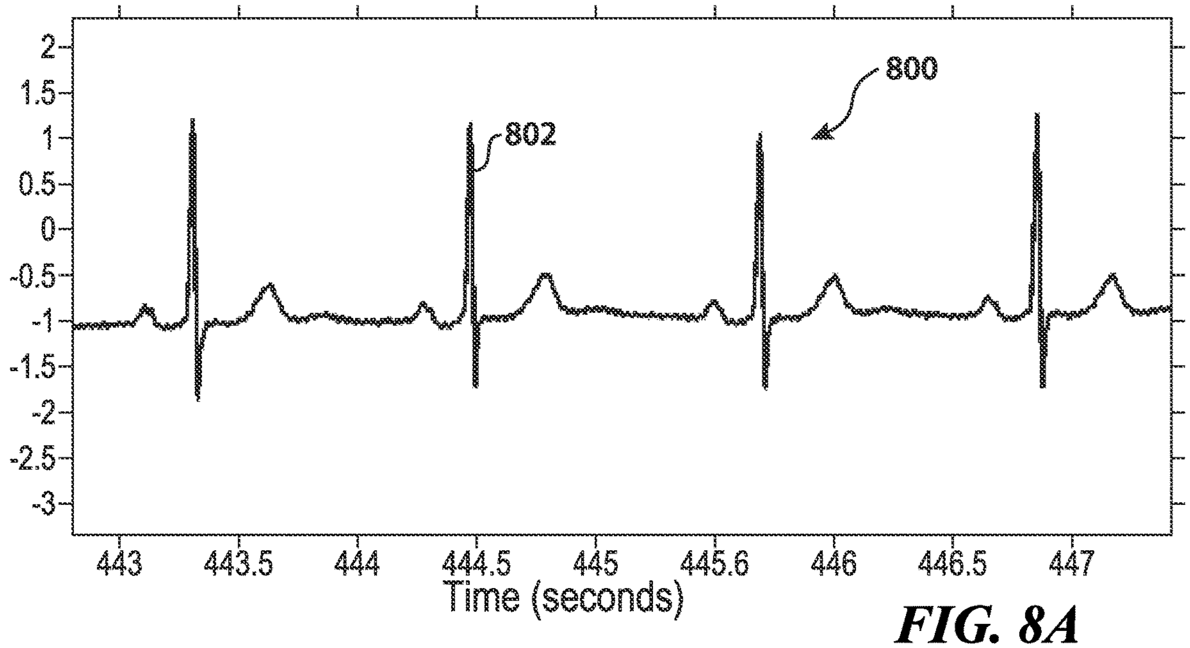
FIG. 8A illustrates a plot of an exemplary ECG signal in accordance with some embodiments of the present technology.
Figure 8B:
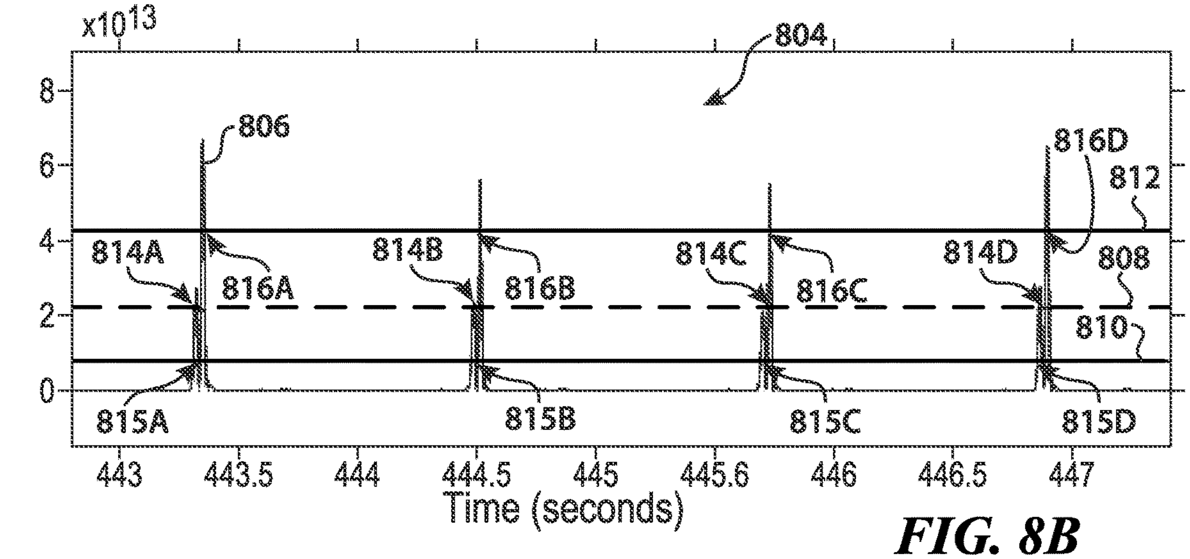
FIG. 8B illustrates a plot of an exemplary filtered ECG signal associated with the ECG signal of FIG. 8A, the exemplary plot further depicting a plurality of R-wave detection threshold values and a plurality of crossings in accordance with some embodiments of the present technology.

FIG. 8A illustrates a plot 800 of an exemplary ECG signal 802 in accordance with some embodiments of the present technology. FIG. 8B illustrates a plot 804 of an exemplary filtered ECG signal 806 associated with ECG signal 802. The plot 804 further depicting a plurality of R-wave detection threshold values 808 and 810, 812 and associated crossings (814 A-D, 815A-D and 816 A-D) of such values by the filtered ECG signal 806. R-wave detection threshold value 808 may be the so-called "single nominal R-wave detection threshold value" described above and associated with a single threshold embodiment. The single nominal R-wave detection threshold value 808 may be set at about 40% of a predicted filtered ECG max value. R-wave detection threshold values 810 and 812 may be the so-called "first and second R-wave detection threshold values" or "speculative and conservative R-wave threshold values" described above and associated with a dual threshold embodiment. The first and second R-wave detection threshold values may be set at about 10% and 60%, respectively, of a predicted filtered ECG max value. In some embodiments, use of a single nominal R-wave detection threshold value (as compared to use of dual R-wave detection threshold values) may cause a delayed detection. For example, in FIG. 8A, the detection may be delayed with respect to the third R-wave because crossing 814C occurs well after crossing 815C.

Predicted Filtered ECG Max Value

Figure 9:
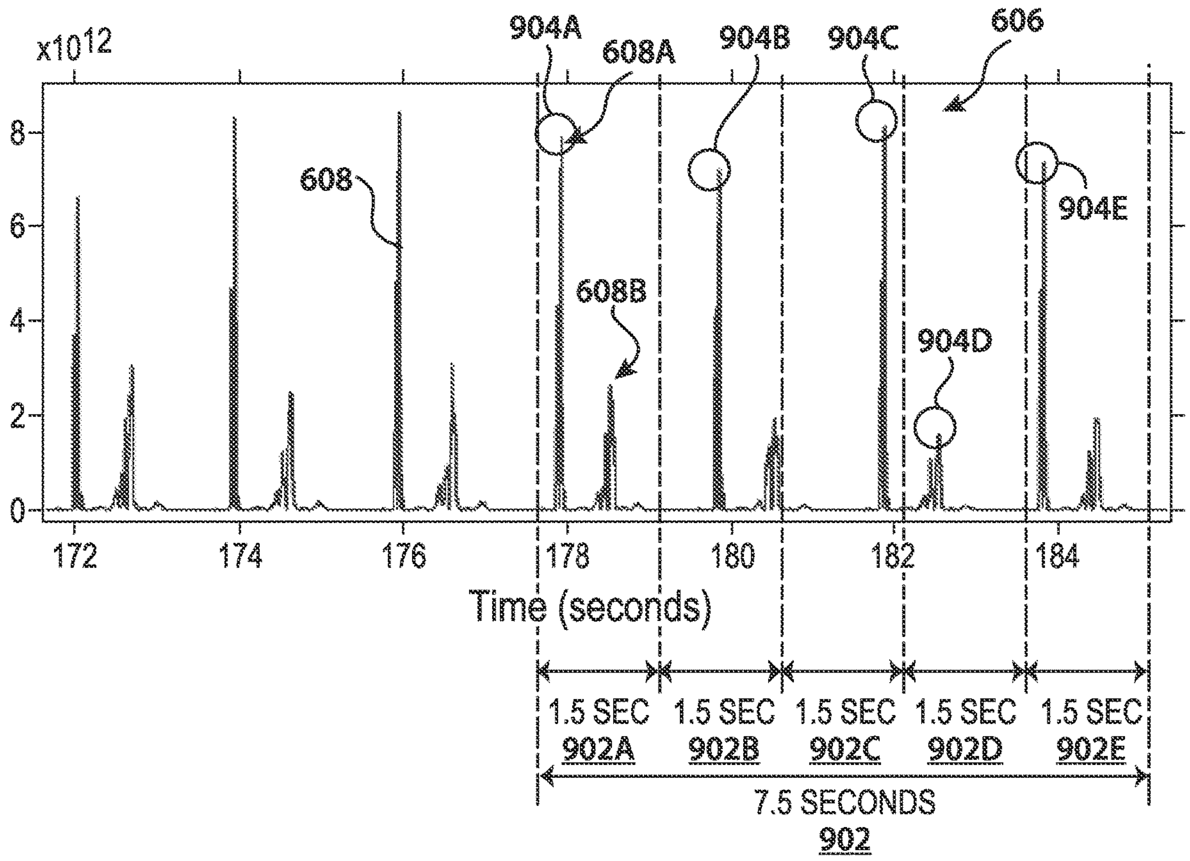
FIG. 9 illustrates the exemplary filtered ECG signal of FIG. 6B together with an exemplary windowing technique capable of detecting filtered ECG max values in each window that may be used to determine an exemplary predicted filtered ECG max value in accordance with some embodiments of the present technology.

With reference to FIGS. 4 and 9, drive unit system 400 may include filtered ECG max value module 408 that generates a predicted filtered ECG max value based on one or more actual max values in a filtered ECG signal, or one or more portions thereof. In some embodiments filtered ECG max value module 408 applies a windowing technique to generate a predicted filtered ECG max value. FIG. 9 illustrates plot 606 (i.e., an exemplary filtered ECG signal 608 from FIG. 6) together with an exemplary windowing technique capable of detecting filtered ECG max values 904A-E in accordance with some embodiments of the present technology. Filtered ECG max value module 408 may receive at least one portion 902 of the filtered ECG signal 608, the portion being divided into a plurality of subportions or windows 902A-E. In other embodiments, filtered ECG max value module 408 may generate portion 902 and windows 902A-E. In some embodiments, portion 902 is 7.5 seconds long and each window 902A-E is 1.5 seconds long. Other sizes and the use of more or less windows is contemplated. For example, as is described in connection with FIG. 10D, a portion may be 3 seconds long and have two (2) 1.5 second windows may be employed. In such embodiments, the use of less windows will allow the filtered ECG max value module 408 to be more responsive to changes in a patient's ECG. In some embodiments, the size of the portion and the number and size of the windows may be selected to ensure that at least some windows will contain a peak that is associated with an R-wave. In some embodiments, the size of the portion and the number and size of the windows may be selected to ensure that at least half of the windows or most (i.e., more than half) of the windows contain a peak that is associated with an R-wave.

Returning to FIG. 9, filtered ECG max value module 408 may detect a max value 904A-E of the filtered ECG signal 608 in each window 902A-E. The filtered ECG max value module 408 may then generate the predicted filtered ECG max value based on one or more of the detected filtered ECG max values 904A-E. For example, the predicted filtered ECG max value may be a mean of, a median of, the minimum of, or the maximum of one or more of the detected filtered ECG max values 904A-E.

The filtered ECG max module 408 may generate a predicted filtered ECG max value on an ongoing basis, on a periodic basis (e.g., during a learning state), or on any combination of the foregoing. The filtered ECG signal 904 may be current or historical or some combination of both current and historical filtered ECG signal 904.

The R-wave detection threshold values described above (single/nominal, first/speculative and second/conservative) may be based on the predicted filtered ECG max value. For example, the R-wave detection threshold values may be a percentage of the predicted filtered ECG max values. First or speculative R-wave detection threshold value may be a first percentage of the predicted filtered ECG max value and second or conservative R-wave detection threshold value may be a second percentage of the predicted filtered ECG max value. The second percentage may be greater than the first percentage. In one embodiment, the first R-wave detection threshold value is between about 7% and about 30% of the predicted filtered ECG max value and the second R-wave detection threshold value is between about 30% and about 60% of the predicted filtered ECG max value. For purposes of the present disclosure the term "about" means, with reference to percentages of other numbers or ranges of numbers, that the percentage can vary by up to 2 percentage points. Accordingly, in the foregoing sentence, the first R-wave detection threshold may be between 5-9% and 28-34% of the predicted filtered ECG max value. Similarly, the second R-wave detection threshold value may be between 28-32% and 58-62% of the predicted filtered ECG max value.

In some embodiments drive unit system 400 includes a GUI 410 wherein a clinician can adjust the R-wave detection threshold values as device settings to customize and make counterpulsation more efficient for each patient. In some embodiments, the clinician may select the desired setting based on observation of a current or historical ECG signal associated with the patient. R-wave detection module 402 may generate the first and second R-wave detection threshold values or the single R-wave threshold value based on default settings and/or based on input from GUI 410. For example:

(a) for patients with few PVCs (e.g., where no more than 5% of the R-waves in the ECG as PVCs) and no history of a-fib and for patients with a normal sinus rhythm, a clinician may adjust the system settings such that the first R-wave detection threshold value is approximately 15% of the predicted filtered ECG max value and the second R-wave detection threshold value is about 50% of the predicted filtered ECG max value;

(b) for patients with a-fib or frequent PVCs (e.g., where at least 20% of the R-waves in the ECG are PVCs), a clinician may adjust the system settings such that the first R-wave detection threshold value is about 7% of the predicted filtered ECG max value and the second R-wave detection threshold value is about 60% of the predicted filtered ECG max value;

(c) for patients with P-waves or T-waves similar in amplitude to R-waves (e.g., where the amplitude of one or more P-waves or T-waves is about 90% of the max amplitude of an R-wave within a predefined window of time, such as 5 seconds) but no arrhythmia, a clinician may adjust the system settings such that the first R-wave detection threshold value is about 30% of the predicted filtered ECG max value and the second R-wave detection threshold value is about 60% of the predicted filtered ECG max value; and (d) for patient with large variations in R-wave amplitude (e.g., where there is a 50% or more change—increase or decrease—in the max amplitude among R-waves within a predefined window of time, such as 5 seconds), a clinician may adjust the system settings such that the first R-wave detection threshold value is about 10% of the predicted filtered ECG max value and the second R-wave detection threshold value is about 30% of the predicted filtered ECG max value.

In certain embodiments, drive unit system 400 includes a noise estimator module 412 operative to generate noise data indicative of the presence of noise (e.g., noise that may interfere with R-wave detection as described above). The source of such noise may be pectoral muscle activity and/or electric circuitry in the vicinity of the patient. Noise estimator module 412 may generate noise data based on information, data, or signals from sensors 160 (e.g., electronic sound transducer sensors). The R-wave detection module 402 may adjust the first/speculative, second/conservative, or single/nominal R-wave detection threshold value based on the generated noise data. For example, R-wave detection module 402 may adjust (e.g., increase) any or all of the R-wave detection threshold values for the duration of any noise. In other embodiments, R-wave detection module 402 may generate the first, second or single R-wave detection threshold values based on the predicted filtered ECG max value and the noise data.

In other embodiments, noise estimator module 412 may generate noise data based on the filtered ECG signal. For example, noise estimator module 412 may employ a windowing technique to generate an ambient noise value based on a filtered ECG signal. The windowing technique may be similar to the windowing technique described above with respect to the filtered ECG max value module 408.

Figure 10A:
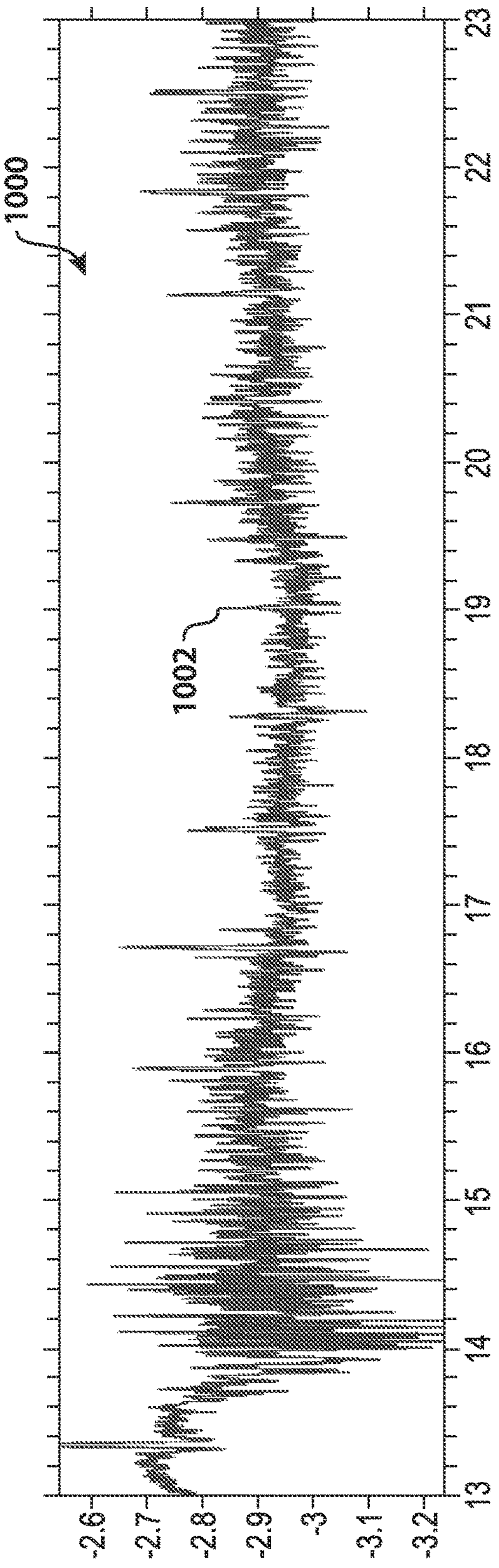
FIG. 10A illustrates an exemplary noisy ECG signal received by the drive unit system of FIG. 4 in accordance with some embodiments of the present technology.
Figure 10B:
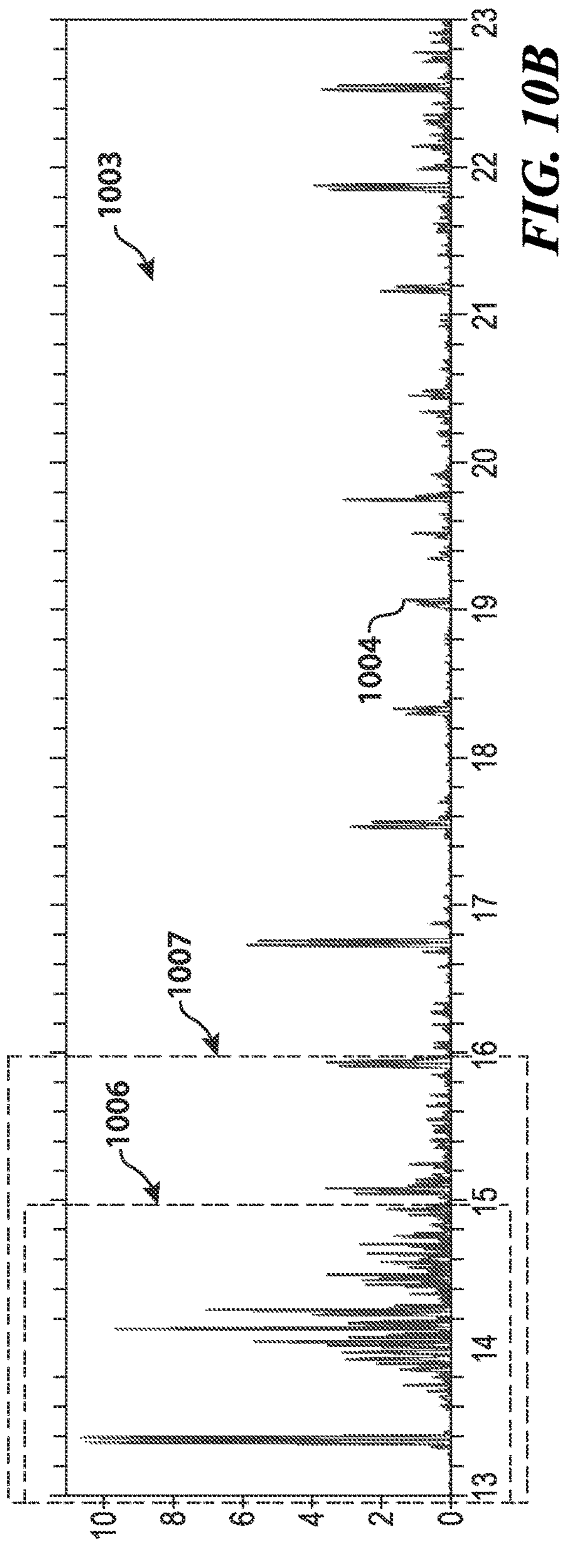
FIG. 10B illustrates an exemplary filtered ECG signal corresponding to the noisy ECG signal of FIG. 10A, in accordance with some embodiments of the present technology.
Figure 10C:
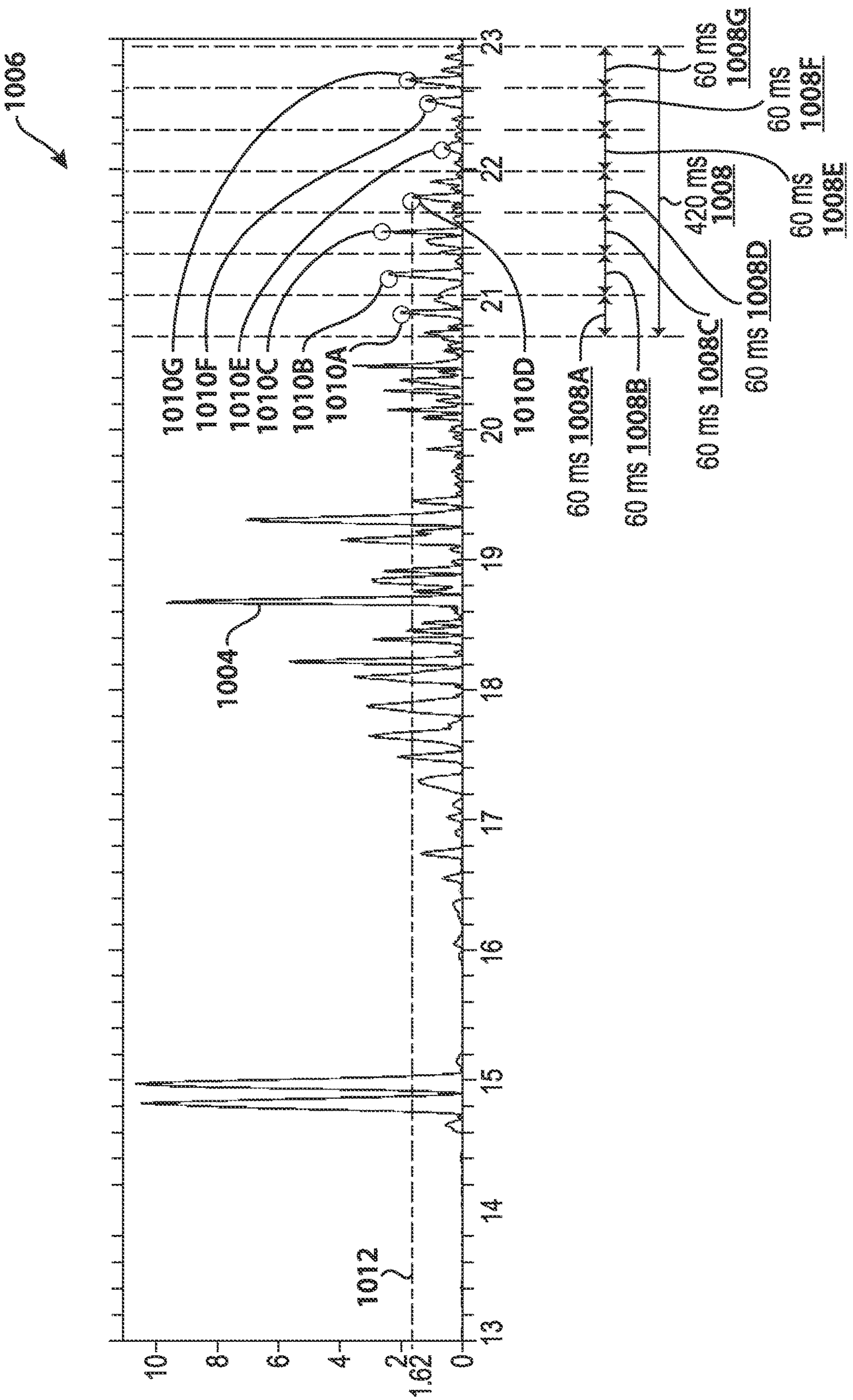
FIG. 10C illustrates an enlarged segment of the exemplary filtered ECG signal of FIG. 10B and a windowing technique to ascertain an exemplary noise bias in accordance with some embodiments of the present technology.
Figure 10D:
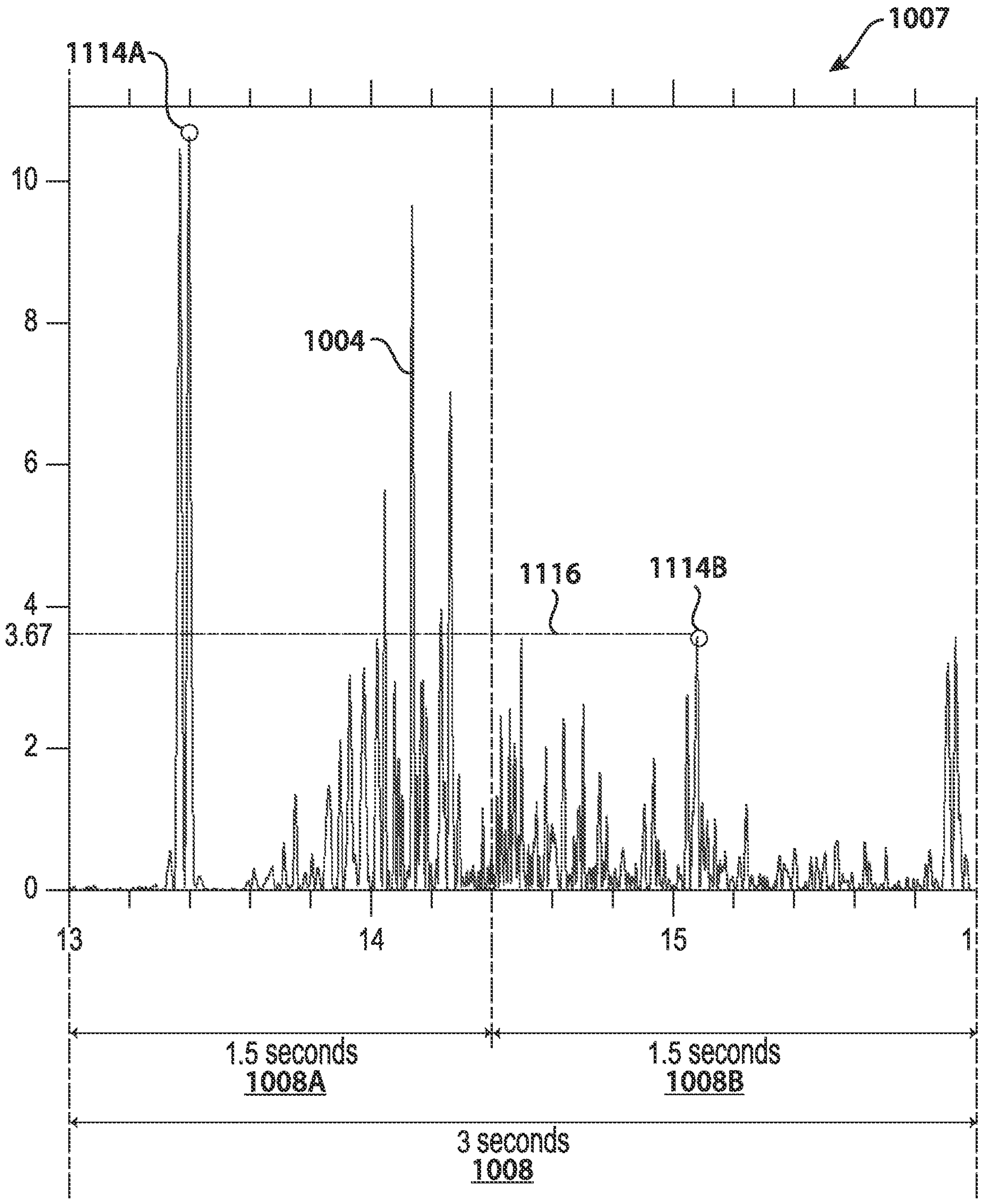
FIG. 10D is a plot of an enlarged segment of the exemplary filtered ECG signal of FIG. 10B together with an exemplary windowing technique capable of detecting filtered ECG max values in each window that may be used to determine an exemplary predicted filtered ECG max value in accordance with some embodiments of the present technology.
Figure 10E:
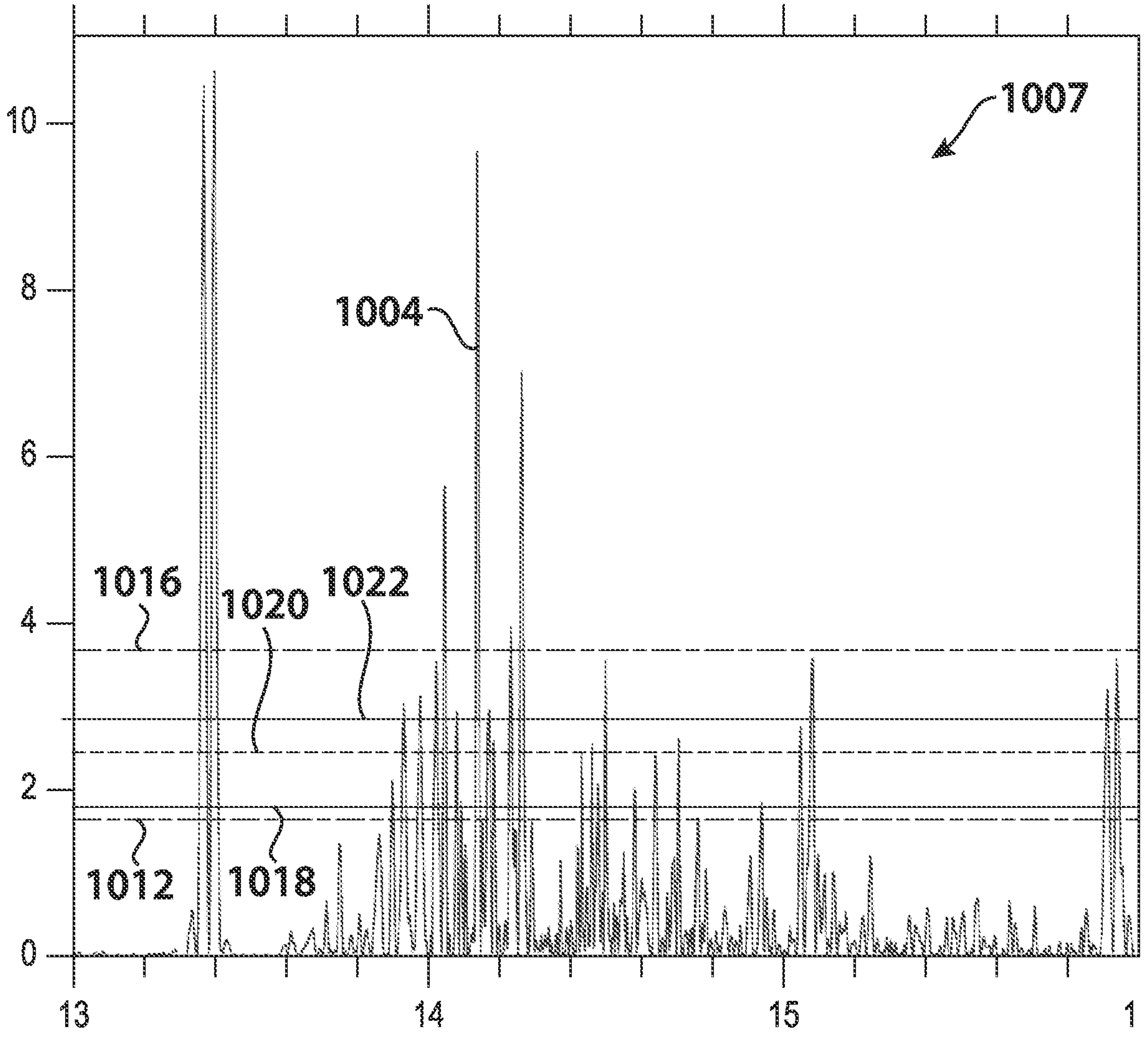
FIG. 10E is a plot of an enlarged segment of exemplary filtered ECG signal of FIG. 10B depicting an ambient noise value, predicted filtered ECG max value, and single, speculative and conservative R-wave detection threshold values, in accordance with some embodiments of the present invention.

FIG. 10A depicts a plot 1000 of an exemplary "noisy" ECG signal 1002. FIG. 10B depicts a plot 1003 of the corresponding filtered ECG signal 1004. Filtered ECG signal 1004 may be generated using filter module 406, as is described above. FIG. 10C is an enlarged view of a first segment 1006 of the filtered ECG signal 1004 and FIGS. 10D and 10E are enlarged views of a second segment 1007 of the filtered ECG signal 1004.

With reference to FIGS. 10A-10E, noise estimator module 412 may obtain a portion 1008 of a filtered ECG signal 1002 having a plurality of subportions or windows 1008A-G. Alternatively, noise estimator module 412 may generate portion 1008 and associated windows 1008A-G. Portion 1008 may be 420 ms long and the plurality of windows 1008A-G may include 7 windows, each 60 ms long. The size of the portion and the number and size of the windows may vary. In some embodiments, the size of the portion and the number and size of the windows may be selected to ensure that at least some windows will not contain a peak associated with an R-wave. In some embodiments, the size of the portion and the number and size of the windows may be selected to ensure that at least half of the windows or most (i.e., more than half) of the windows contain a peak that is not associated with an R-wave. For example, by selecting a portion sized at 420 ms and by employs 7 windows that are each 60 ms long, it is assumed that for a heart rate up to 200 bpm, no more than three subportions or windows will contain a peak associated with an R-wave.

With reference to FIG. 10C, for each window 1008A-D, the noise estimator module 412 may detect a filtered ECG max value 1010A-G. Noise estimator module 412 may generate the ambient noise value as a function of one or more of the detected max values 1010A-G. For example, the ambient noise value may be a mean, a median, or the minimum of such detected max values 1010A-G. In the example illustrated in FIG. 10C, the noise estimator module 412 is configured such that the ambient noise value is the median of the seven detected max values 1010A-G. Using the data in this illustration, the ambient noise value in FIG. 10C corresponds to max value 101D.

The noise estimator module 412 may generate the ambient noise value on an ongoing basis, on a periodic basis (e.g., during a learning state), or on any combination of the foregoing. The filtered ECG signal used to generate the ambient noise value may be current or historical or some combination of both a current and historical filtered ECG signal.

Filtered ECG max value module 408 may perform its own windowing technique on the same or another portion of the filtered ECG signal 1004 to generate the predicted filtered ECG max value. For example and with respect to FIG. 10D, which illustrates a enlarged plot of segment 1007 of filtered ECG signal 1004, filtered ECG max value module 408 may generate the predicted filtered ECG max value based on portion 1008 and windows 1008A-1008B. In one embodiment, portion 1008 is 3 seconds long and each windows 1008A-B is 1.5 seconds long. The predicted filtered ECG max value may be based on one or more of the max values in windows 1008A-B. In some embodiments, the predicted filtered ECG max value may be a mean of, the minimum of or the maximum of the detected max values. In the example illustrated in FIG. 10D, the filtered ECG max value module 408 is configured such that the predicted filtered ECG max value is the minimum of the detected max values. Using the data in this illustration, the predicted filtered ECG max value in FIG. 10C corresponds to detected max value 1114B.

In some embodiments, R-wave detection module 402 may generate one or more R-wave detection threshold values based on the predicted filtered ECG max value and the ambient noise value 1012. In some embodiments, the ambient noise value serves as a bias. In some embodiments, the R-wave detection threshold values may be the sum of (1) the ambient noise value and (2) the product of a weighted difference between the predicted filtered ECG max value 1016 and the ambient noise threshold value 1012). In equation format, the R-wave detection threshold value is set out in equation 1.0, where "RDTV" is the R-wave detection threshold value, "ANV" is the ambient noise value, "n" is the weighting factor, and "PMV" is the predicted filtered ECG max value:

$$RDTV = ANV + \{n \cdot (PMV - ANV)\} \quad \text{(Eqn. 1.0)}$$

The weighting factor (i.e., "n" in Eqn 1.0) may be about 40% for embodiments where a single/nominal R-wave detection threshold value is used to detect the R-waves. Alternatively, in embodiments that employ dual R-wave detection threshold values, the weighting factor for the first/speculative R-wave detection threshold value may be between about 7 and 30% and the weighting factor for the second/conservative R-wave detection threshold value may be between about 30 and 60%.

In embodiments where drive unit system 400 includes a GUI 410 wherein a clinician can adjust the R-wave detection threshold values as device settings to customize and make counterpulsation more efficient for each patient. In some embodiments, the clinician may select the desired setting based on observation of a current or historical ECG signal associated with the patient. R-wave detection module 402 may generate the first and second R-wave detection threshold values or the single R-wave threshold value based on default settings and/or based on input from GUI 410. For example:

(a) for patients with few PVCs (e.g., where no more than 5% of the R-waves in the ECG as PVCs) and no history of a-fib and for patients with a normal sinus rhythm, a clinician may adjust the system settings such that the weighting factor for the first R-wave detection threshold value is about 15% and the weighting factor for the second R-wave detection threshold value is about 50%;

(b) for patients with a-fib or frequent PVCs (e.g., where at least 20% of the R-waves in the ECG are PVCs), a clinician may adjust the system settings such that the weighting factor for the first R-wave detection threshold value is about 7% and the weighting factor for the second R-wave detection threshold value is about 60%;

(c) for patients with P-waves or T-waves similar in amplitude to R-waves (e.g., where the amplitude of one or more P-waves or T-waves is about 90% of the max amplitude of an R-wave within a predefined window of time, such as 5 seconds) but no arrhythmia, a clinician may adjust the system settings such that the weighting factor for the first R-wave detection threshold value is about 30% and the weighting factor for the second R-wave detection threshold value is about 60%; and (d) for patient with large variations in R-wave amplitude (e.g., where there is a 50% or more change—increase or decrease—in the max amplitude among R-waves within a predefined window of time, such as 5 seconds), a clinician may adjust the system settings such that the weighting factor for the first R-wave detection threshold value is about 10% and the weighting factor for the second R-wave detection threshold value is about 30%.

FIG. 10E illustrates enlarged segment 1007 of filtered ECG signal 1004 against exemplary ambient noise value 1012 (as determined in FIG. 10C), predicted filtered ECG max value 1016 (as determined in FIG. 10D), and exemplary first, single and second R-wave detection threshold values 1018, 1020 and 1022, respectively. Single R-wave detection threshold value 1020 was based on a 40% weighting factor, first R-wave detection threshold value 1018 was based on a 7% weighting factor, and second R-wave detection threshold value 1022 was based on a 60% weighting factor.

Deflation Trigger

As noted above, deflation of the balloon may be based on a deflation trigger. A deflation trigger may be based on either the single/nominal detection (e.g., in embodiments where there is a single R-wave detection threshold value) or speculative detection (e.g., in embodiments where there are dual R-wave detection threshold values). In some embodiments, the deflation trigger is the single detection or the speculative detection. In other embodiments, the deflation trigger is the first to occur of (1) the single detection or the speculative detection (based on the embodiment), and (2) an expiration of a predicted R-to-R time interval. The predicted R-to-R time interval may represent a time in which an R-wave is "expected" or "predicted to be detected." In embodiments where there is a single R-wave detection threshold value, the predicted R-to-R time interval may be measured from the last (e.g., most immediate previous) single/nominal detection, e.g., detection 710. In embodiments where there are two R-wave detection threshold values, the predicted R-to-R time interval may be measured from the last (e.g., most immediate previous) conservative detection, e.g., conservative detection 714.

In some embodiments, drive unit system 400 includes an R-to-R interval module 414 that generates the predicted R-to-R time interval based on the filtered ECG signal (e.g., from filter module 406). For example, with reference to FIG. 8B, the predicted R-to-R time interval may be based on the time between single/nominal detections 814A-D or the time between conservative detections 816A-D. In some embodiments, the predicted R-to-R time interval is a mean or a median of the time between a plurality of such past detections.

In other embodiments, R-to-R interval module 414 operates similar to filtered ECG max value module 408 (or is part of the same module), but adds functionality associated with detecting the time of each filtered ECG max value 904A-E. The predicted R-to-R time interval may be a function of such detected times. For example, the predicted R-to-R time interval may be the mean or the median of such detected times.

In embodiments where the deflation trigger is the first to occur of (1) a detection (single/nominal or conservative) and (2) an expiration of a predicted R-to-R time interval, the latter component ensures that the balloon pump 110 is deflated if the technology misses an R-wave.

Inflation

Drive unit 404 may cause the balloon pump 110 to inflate based on the single/nominal detection (e.g., detection 710 or any of detections 814A-D) or based on the conservative detection (e.g., detection 714 or any of detections 816A-D). In some embodiments, drive unit 404 inflates balloon pump 110 based on the time of the applicable detection and a predicted QS2 timing interval. As indicated in FIG. 3, a QS2 timing interval 330 is the interval of time from the beginning of the Q-wave 206 to the S2 heart sound 326. A predicted QS2 timing interval may approximate the actual QS timing interval 330. In some embodiments, drive unit 404 inflates balloon pump 110 at or about at a time equal to a detection (e.g., a single detection or a conservative detection) plus the predicted QS2 time interval.

In some embodiments, the predicted QS2 timing interval is empirically obtained based on scientific studies. In other embodiments, the predicted QS2 timing interval is specific to the patient. For example, predicted QS2 time interval may be obtained using a phonocardiograph system (not depicted) that is able to detect the S2 heart sounds 326 and the time of each such detection. In other embodiments and with reference to FIG. 4, drive unit system 400 may include a QS2 time interval module 416 that generates the predicted QS2 timing interval based on pressure data sensed by sensor 160. In some embodiments, the drive unit system 400 pauses counterpulsation and the drive unit 404 partially inflates the balloon pump 110 for one or more cardiac cycles. In certain embodiments the balloon pump 110 is inflated to about 50% of its volume. During LV systole (i.e., ejection) 302, the balloon pump 110 remains partially inflated and a pressure sensor located in the drive unit 404 senses a change in pressure caused by compression of the balloon pump 110 during systole. Drive unit 404 communicates pressure information to QS2 time interval module 416, which may indirectly detect the dicrotic notch 320 from such pressure information. Based on the time of one or more dicrotic notch 320 detections, QS2 time interval module 416 may generate a predicted QS2 timing interval that represents the time from a detection of the R-wave 208 to a predicted dicrotic notch. In certain embodiments, the predicted QS2 timing interval is based on the time of one or more R-wave detections (e.g., as determined by R-wave detection module 402) and one or more dicrotic notch detections (as determined by QS2 time interval module 416). For example, predicted QS2 timing interval may be mean or a median of the time difference between the occurrence of one or more R-wave detections and one or more dicrotic notch detections.

Figure 11:
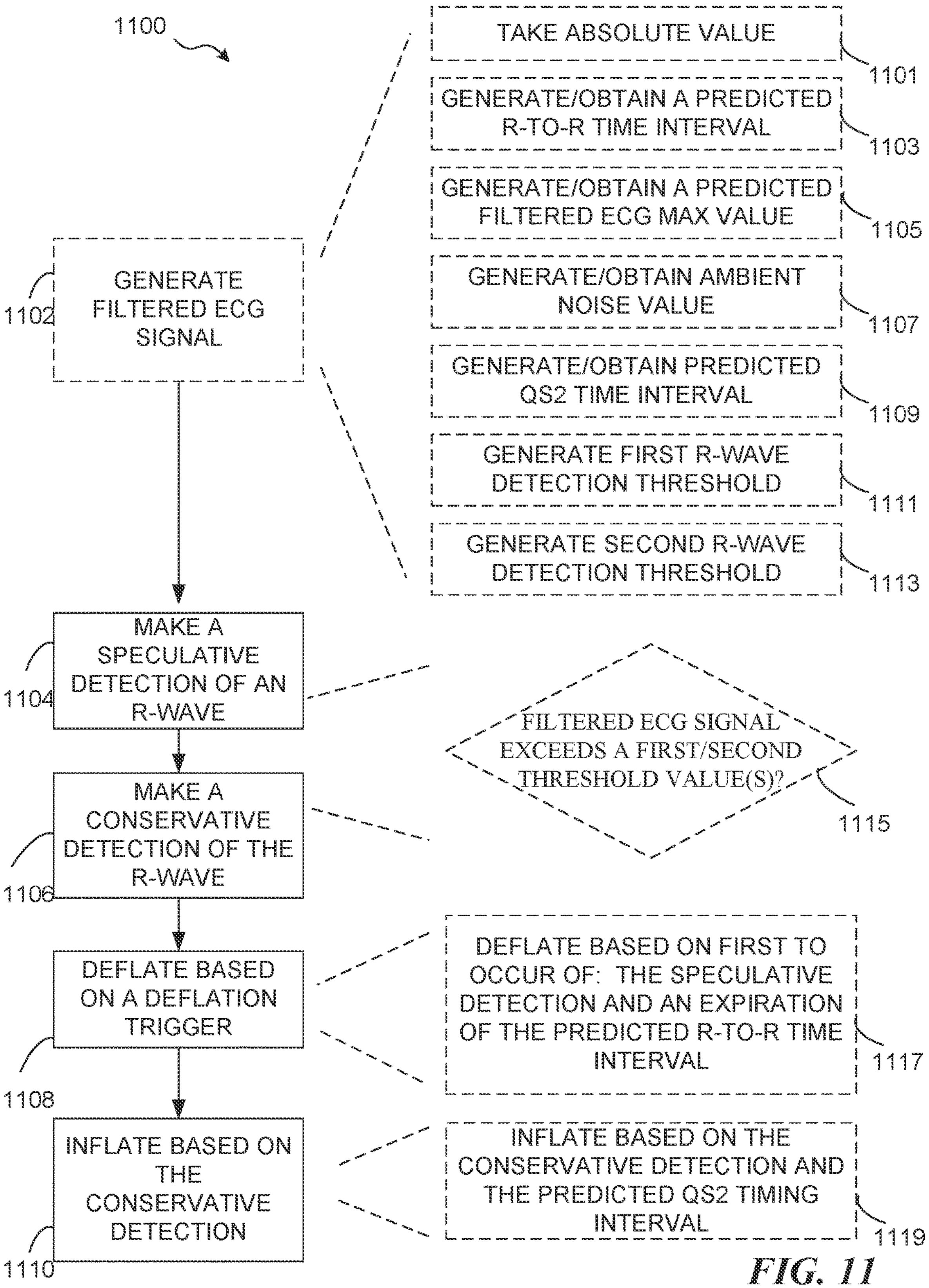
FIG. 11 illustrates an exemplary method for using the drive unit system of FIG. 4 in accordance with some embodiments of the present technology.

FIG. 11 illustrates an exemplary method 1100 for using the drive unit system 400 of FIG. 4 in accordance with some embodiments of the present technology. The method 1100 may include block 1102, where a received filtered ECG signal may be generated. In some embodiments filtered ECG signal may be generated by filter module 406. In some embodiments, the method 1100 may include block 1101 where an absolute value of the filtered ECG signal is obtained. In some embodiments, the absolute value of filtered ECG signal may be obtained by absolute value module 510. Method 1100 may also include block 1103 where a predicted R-to-R time interval is generate or obtained. In some embodiments, the predicted R-to-R time interval may be generated or obtained by R-to-R time interval module 414. Method 1100 may also include block 1105 where a predicted filtered ECG max value is generated or obtained. In some embodiments, the predicted filtered ECG max value is generated or obtained by filtered ECG max value module 408. Method 1100 may also include block 1107 where an ambient noise value is generated or obtained. In some embodiments, ambient noise value is generated or obtained noise estimator module 412. Method 1100 may also include block 1109 where a predicted QS2 time interval may be generated or obtained. In some embodiments, a predicted QS2 time interval may be generated or obtained by QS2 time interval module 416. Method 1100 may include blocks 1111 and 1113 where first and second R-wave detection values are generated or obtained, respectively. In some embodiments, the first and second R-wave detection values are generated or obtained by R-wave detection module 402. In some embodiments, first and second R-wave detection values are based on the predicted filtered ECG max value. In some embodiments, first and second R-wave detection values are based on the predicted filtered ECG max value and the ambient noise value.

Method 1100 may include block 1104 where a speculative detection of an R-wave is made and block 1106 where a conservative detection of an R-wave is made. In some embodiments, the speculative and conservative detections may be made by R-wave detection module 402. Method 1100 may include block 1115 where it is determined whether filtered ECG signal exceeds or crosses a first and/or a second R-wave threshold value. In some embodiments, this determination may be made by R-wave detection module 402.

Method 1110 may include block 1108 where the balloon pump 110 may be deflated based on a deflation trigger. In some embodiments, deflation is caused by drive unit 404. Method 1110 may include block 1107 where deflation is based on the first to occur of the speculative detection and an expiration of the predicted R-to-T time interval. In some embodiments, such deflation is caused by drive unit 404.

Finally, the method 1100 may include block 1110 where the balloon pump 110 may inflated based on the conservative detection. In some embodiments, inflation is caused by drive unit 404. Method 1100 may include block 1119 where the balloon pump 110 is inflated based on the conservative detection and the predicted QS2 timing interval. In some embodiments, such inflation is caused by drive unit 404.

Figure 12:
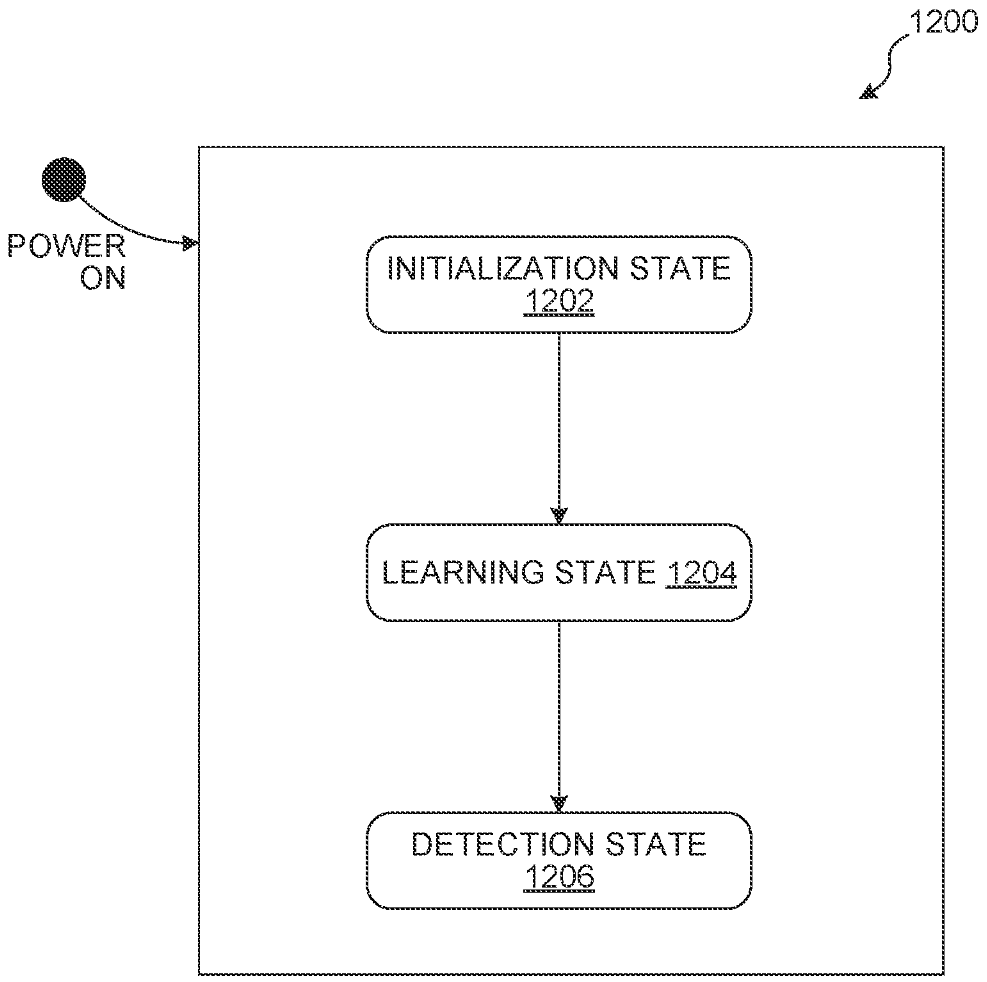
FIG. 12 illustrates a state diagram of the drive unit system of FIG. 4 in accordance with some embodiments of the present technology.

FIG. 12 illustrates an exemplary state diagram 1200 of the drive unit system 400 in accordance with some embodiments of the present technology. State diagram 1200 may include three states: initialization state 1202, learning state 1204 and detection state 1206. During initialization state 1202, ECG signals and sensor data may be initialized and received. Learning state 1204 may be associated with method blocks 1102, 1101, 1103, 1105, 1107, 1109, 1111 and 1113. Detection state 1206 may be associated with method blocks 1104, 1106, 1115, 1108, 1117, 1110, and 1119. In some embodiments, detection state 1206 may be associated with all method blocks (e.g., where parameters and values may be continuously updated).

The technology and techniques described herein offer efficient and effective detection of R-waves for use by CADs, including but not limited to counterpulsation devices. When employing dual R-wave detection thresholds, the present technology minimizes both missed R-waves (thereby reducing the chance of the balloon pump 110 staying inflated too long) and false detections (thereby reducing the chance the balloon pump 110 inflates too early, resisting ejection during systole). Although the foregoing technology was described with reference to counterpulsation devices in particular, the technology may be readily applied to other CADS operating in co- or counterpulsation modalities. For example, whereas the foregoing referred to inflation of an IABP during diastole and deflation of an IABP during systole, one of skill in the art will readily appreciate that inflation of an IABP increases aortic blood pressure and deflation decreases aortic blood pressure. Accordingly, the foregoing technology may be applied to any manner of CADs, including CADs that operate in co- and counterpulsation modalities that operate to increase or decrease aortic blood pressure in synchrony with the heart. For example the foregoing technology may be used to determine when a VAD operating in a copulsation modality should increase aortic blood pressure (i.e., during systole) and when to decrease aortic blood pressure (i.e., during diastole).

As used herein, "module" may refer to any single or collection of circuit(s), integrated circuit(s), hardware processor(s), processing device(s), transistor(s), non-transitory memory(s), storage devices(s), non-transitory computer readable medium(s), combination logic circuit(s), or any combination of the above that is capable of providing a desired operation(s) or function(s). For example, "module" may take the form of a hardware processor executing instructions from one or more non-transitory memories, storage devices, or non-transitory computer readable media, or a dedicated integrated circuit. "Non-transitory memory," "non-transitory computer-readable media," and "storage device" may refer to any suitable internal or external non-transitory, volatile or non-volatile, memory device, memory chip(s), or storage device or chip(s) such as, but not limited to system memory, frame buffer memory, flash memory, random access memory (RAM), read only memory (ROM), a register, a latch, or any combination of the above. A "hardware processor" may refer to one or more dedicated or non-dedicated: hardware micro-processors, hardware micro-controllers, hardware sequencers, hardware micro-sequencers, digital signal hardware processors, hardware processing engines, hardware accelerators, applications specific circuits (ASICs), hardware state machines, programmable logic arrays, any integrated circuit(s), discreet circuit(s), etc. that is/are capable of processing data or information, or any suitable combination(s) thereof. A "processing device" may refer to any number of physical devices that is/are capable of processing (e.g., performing a variety of operations on) information (e.g., information in the form of binary data or carried/represented by any suitable media signal, etc.). For example, a processing device may be a hardware processor capable of executing executable instructions, a desktop computer, a laptop computer, a mobile device, a hand-held device, a server (e.g., a file server, a web server, a program server, or any other server), any other computer, etc. or any combination of the above. An example of a processing device may be a device that includes one or more integrated circuits comprising transistors that are programmed or configured to perform a particular task. "Executable instructions" may refer to software, firmware, programs, instructions or any other suitable instructions or commands capable of being processed by a suitable hardware processor.

While illustrative embodiments have been described herein, the scope thereof includes any and all embodiments having equivalent elements, modifications, omissions, combinations (e.g., of aspects across various embodiments), adaptations and/or alterations as would be appreciated by those in the art based on the present disclosure. For example, the number and orientation of components shown in the exemplary systems may be modified.

Those skilled in the art will appreciate that the method depicted in FIG. 11may be altered in a variety of ways. For example, the order of the acts may be rearranged; some acts may be performed in parallel; shown acts may be omitted, or other acts may be included; a shown act may be divided into sub acts, or multiple shown acts may be combined into a single act, etc.

It will be appreciated by those skilled in the art that the above-described facility may be straightforwardly adapted or extended in various ways. While the foregoing description makes reference to particular embodiments, the scope of the invention is defined solely by the claims that follow and the elements recited therein.

What is claimed is:

1. A drive unit system for operating a cardiac assist device, the drive unit system comprising:

an R-wave detection module operative to:

make a speculative detection of an R-wave associated with a received electrocardiogram (ECG) signal of a heart of a patient using a first R-wave detection threshold value; and make a conservative detection of the R-wave associated with the ECG signal using a second R-wave detection threshold value, wherein the second R-wave detection threshold value is greater than the first R-wave detection threshold value; and a drive unit operatively coupleable to the cardiac assist device, the drive unit operative to cause the cardiac assist device to alter aortic blood pressure relative to an unassisted aortic blood pressure based on the speculative detection and the conservative detection.

2. The drive unit system of claim 1, wherein the cardiac assist device is a counterpulsation device.

3. The drive unit system of claim 2, wherein the cardiac assist device is an intra-aortic balloon pump.

4. The drive unit system of claim 3, wherein the drive unit is operative to deflate the intra-aortic balloon pump based on the speculative detection and inflate the intra-aortic balloon pump based on the conservative detection.

5. The drive unit system of claim 2, wherein the drive unit is operative to decrease the aortic blood pressure based on a deflation trigger, wherein the deflation trigger is based on the speculative detection.

6. The drive unit system of claim 5, wherein the deflation trigger is the first to occur of: the speculative detection of the R-wave and an expiration of a predicted R-to-R time interval.

7. The drive unit system of claim 6, wherein the expiration of the predicted R-to-R time interval is measured from the time of a most immediate previous conservative detection of a previous R-wave.

8. The drive unit system of claim 6, the system further comprising an R-to-R time interval module operative to generate the predicted R-to-R time interval based on a filtered ECG signal.

9. The drive unit system of claim 8, wherein the R-to-R time interval module is operative to generate the predicted R-to-R time interval based on a plurality of conservative detections of R-waves.

10. The drive unit system of claim 9, wherein the predicted R-to-R time interval is one of:

a mean of the time between the plurality of conservative detections; and a median of the time between the plurality of conservative detections.

11. The drive unit system of claim 8, wherein the R-to-R time interval module is operative to:

receive at least one portion of the filtered ECG signal divided into a plurality of windows; and for each window, detect a time associated with a max value of the filtered ECG signal within each window, wherein the predicted R-to-R time interval is based on one or more of the plurality of detected times associated with the plurality of max values.

12. The drive unit system of claim 11, wherein the predicted R-to-R time interval is one of:

a mean of one or more of the plurality of detected times; and a median of one or more of the plurality of detected times.

13. The drive unit system of claim 5, wherein the drive unit system further comprises a filter module operative to convert the received ECG signal into a filtered ECG signal.

14. The drive unit system of claim 13, wherein the filter module filters out frequencies that are not associated with an R-wave.

15. The drive unit system of claim 13, wherein the filtered ECG signal approximates an absolute value of a derivative of a smoothed version of the ECG signal.

16. The drive unit system of claim 13, wherein the filter module comprises a bandpass filter.

17. The drive unit system of claim 13, wherein the filter module comprises a weighting filter.

18. The drive unit system of claim 17, wherein a wavelet filter is configured to apply a Haar wavelet function.

19. The drive unit system of claim 17, wherein a wavelet filter is configured to apply a symlet 4 wavelet function.

20. The drive unit system of claim 17, wherein the R-wave detection module is further operative to determine a current value of the filtered ECG signal, and wherein:

the R-wave detection module is operative to make the speculative detection by determining that the current value of the filtered ECG signal exceeds a first R-wave detection threshold value, and the R-wave detection module is operative to make the conservative detection by determining that the current value of the filtered ECG signal exceeds a second R-wave detection threshold value, the second R-wave detection threshold value is greater than the first R-wave detection threshold value.

21. The drive unit system of claim 20, wherein the first and second R-wave detection threshold values are based on a predicted filtered ECG max value.

22. The drive unit system of claim 21, the system further comprising a max filtered ECG value module operative to generate the predicted filtered ECG max value based on a filtered ECG max value in the filtered ECG signal.

23. The drive unit system of claim 21, wherein a max filtered ECG value module is operative to generate the predicted filtered ECG max value by:

receiving at least one portion of the filtered ECG signal divided into a plurality of windows; and for each window, detecting a max value of the filtered ECG signal within each window.

24. The drive unit system of claim 23, wherein the predicted filtered ECG max value is one of:

a mean of the one or more detected max values;

a median of the one or more detected max values;

a minimum of the one or more detected max values; and a maximum of the one or more detected max values.

25. The drive unit system of claim 21, wherein:

the first R-wave detection threshold value is a first percentage of the predicted filtered ECG max value, the second R-wave detection threshold value is a second percentage of the predicted filtered ECG max value, and the second percentage is greater than the first percentage.

26. The drive unit system of claim 21, wherein the first and second R-wave detection threshold values are based on the predicted filtered ECG max value and an ambient noise value.

27. The drive unit system of claim 26, the system further comprising a noise estimator module operative to generate the ambient noise value based on the filtered ECG signal.

28. The drive unit system of claim 27, wherein the noise estimator module is operative to generate the ambient noise value by:

receiving at least one portion of the filtered ECG signal divided into a plurality of windows; and for each window, detecting a max value of the filtered ECG signal within each window.

29. The drive unit system of claim 28, wherein the ambient noise value is one of:

a mean of the one or more detected max values;

a median of the one or more detected max values; and a minimum of the one or more detected max values.

30. The drive unit system of claim 13, wherein the filter module comprises a wavelet filter.

31. The drive unit system of claim 30, wherein the wavelet filter is operative to:

decompose at least a portion of the ECG signal into a plurality of discrete frequency signals; and aggregate a signal based on one or more of the decomposed signals.

32. The drive unit system of claim 31, wherein the one or more of the decomposed signals have frequencies that are associated with an R-wave.

33. The drive unit system of claim 31, wherein the filter module comprises an absolute value module operative to generate the filtered ECG signal by taking an absolute value of one of: the aggregated signal and the one or more of the decomposed signals.

34. The drive unit system of claim 30, wherein the wavelet filter comprises a discrete wavelet transformation module and an aggregator module.

35. The drive unit system of claim 34, wherein:

the discrete wavelet transformation module is operative to perform a discrete wavelet multistep decomposition of the ECG signal using a wavelet transform function at a plurality of levels, thereby generating wavelet approximation (a) and detail (d) coefficients at each such level; and the aggregator module is operative to generate an aggregated signal by aggregating one or more coefficients.

36. The drive unit system of claim 35, wherein at least one or more of the levels of the plurality of levels are associated with frequencies that are associated with an R-wave.

37. The drive unit system of claim 13, wherein the R-wave detection module is operative to:

make the speculative detection based on the filtered ECG signal; and make the conservative detection based on the filtered ECG signal.

38. The drive unit system of claim 5, wherein the drive unit is operative to inflate a balloon pump based on a QS2 timing interval.

39. The drive unit system of claim 38, wherein the QS2 time interval is empirically obtained.

40. The drive unit system of claim 38, wherein the predicted QS2 time interval is specific to the patient.

41. The drive unit system of claim 40, wherein the drive unit system further comprises a QS2 time interval module operative to generate a QS2 time interval based on pressure data obtained via a pressure sensor associated with the drive unit.

42. The drive unit system of claim 41, wherein the QS2 time interval is based on pressure changes caused by ejection of blood during systole on a partially inflated balloon pump.

43. The drive unit system of claim 38, wherein the drive unit is operative to inflate the balloon based on the conservative detection and the QS2 time interval.

44. The drive unit system of claim 38, wherein the QS2 timing interview is a predicted QS2 timing interval.

45. The drive unit system of claim 5, wherein drive unit is operative to cause a balloon pump to be 50% deflated in about 100-120 ms of the deflation trigger and fully deflated in about 140-180 ms of the deflation trigger.

46. The drive unit system of claim 1, wherein the cardiac assist device is a ventricle assist device (VAD) operated in a counterpulsation modality.

47. The drive unit system of claim 1, wherein the drive unit is operative to decrease the aortic blood pressure relative to the unassisted aortic blood pressure based on the speculative detection, and increase the aortic blood pressure relative to the unassisted aortic blood pressure based on the conservative detection.

48. The drive unit of claim 1, wherein the cardiac assist device is a ventricle assist device (VAD) operated in a copulsation modality.

49. The drive unit system of claim 48, wherein the second R-wave detect threshold value is later in time than the first R-wave detection threshold value.

50. The drive unit system of claim 1, wherein the first and second R-wave detection thresholds values are based on a predicted ECG max value.

51. A drive unit system for operating a counterpulsation device, the drive unit system comprising:

an R-wave detection module operative to:

make a speculative detection of an R-wave associated with a received electrocardiogram (ECG) signal of a heart of a patient; and make a conservative detection of the R-wave associated with the ECG signal; and a drive unit operatively coupleable to the counterpulsation device, the drive unit operative to:

operate the counterpulsation device based on the speculative detection and the conservative detection; and decrease the aortic blood pressure based on a deflation trigger, the deflation trigger being based on the speculative detection; and a filter module operative to convert the received ECG signals into a filtered ECG signal, the filter module at least one of: (1) configured to filter out frequencies that are not associated with an R-wave, or (2) including a bandpass filter, a weighting filter, or a wavelet filter.

52. The drive unit system of claim 51, wherein the filter module includes a wavelet filter, the wavelet filter at least one of (1) is operative to decompose at least a portion of the ECG signal into a plurality of discrete frequency signals and aggregate a signal based on one or more of the decomposed signals, (2) includes a discrete wavelet transformation module and an aggregator module, or (3) is configured to apply a symlet 4 wavelet function.

53. A drive unit system for operating a counterpulsation device, the drive unit system comprising:

an R-wave detection module configured to:

make a speculative detection of an R-wave associated with a received electrocardiogram (ECG) signal of a heart of a patient; and make a conservative detection of the R-wave associated with the ECG signal; and a drive unit operatively coupleable to the counterpulsation device, the drive unit configured to:

operate the counterpulsation device based on the speculative detection and the conservative detection;

decrease the aortic blood pressure based on a deflation trigger, the deflation trigger being based on the speculative detection; and inflate a ballon pump based on a QS2 time interval.

54. The drive unit system of claim 53, wherein the QS2 time interval is at least one of empirically obtained or specific to the patient.

55. The drive unit system of claim 53, wherein the drive unit is operative to inflate the balloon based on the conservative detection and the QS2 time interval.

56. The drive unit system of claim 53, wherein the QS2 time interview is a predictive QS2 time interval.

57. A drive unit system for operating a counterpulsation device, the drive unit system comprising:

an R-wave detection module configured to:

make a speculative detection of an R-wave associated with a received electrocardiogram (ECG) signal of a heart of a patient; and make a conservative detection of the R-wave associated with the ECG signal; and a drive unit operatively coupleable to the counterpulsation device, the drive unit configured to:

operate the counterpulsation device based on the speculative detection and the conservative detection;

decrease the aortic blood pressure based on a deflation trigger, the deflation trigger being based on the speculative detection; and cause a balloon pump to be 50% deflated in about 100-120 ms of the deflation trigger and fully deflated in about 140-180 ms of the deflation trigger.

* * * * *